United States Patent
Garland et al.

(10) Patent No.: US 12,109,222 B2
(45) Date of Patent: *Oct. 8, 2024

(54) METHODS AND COMPOSITIONS FOR TREATING MUCOSITIS

(71) Applicant: Tosk, Inc., Mountain View, CA (US)

(72) Inventors: William A. Garland, Mountain View, CA (US); Brian D. Frenzel, Mountain View, CA (US); Philip Liaw, San Jose, CA (US)

(73) Assignee: Tosk, Inc., Mountain View, CA (US)

( * ) Notice: Subject to any disclaimer, the term of this patent is extended or adjusted under 35 U.S.C. 154(b) by 673 days.

This patent is subject to a terminal disclaimer.

(21) Appl. No.: 17/175,258

(22) Filed: Feb. 12, 2021

(65) Prior Publication Data

US 2021/0236530 A1   Aug. 5, 2021

Related U.S. Application Data

(63) Continuation-in-part of application No. PCT/US2019/046386, filed on Aug. 13, 2019.

(60) Provisional application No. 62/718,831, filed on Aug. 14, 2018.

(51) Int. Cl.
*A61K 31/7072* (2006.01)
*A61K 31/519* (2006.01)
*A61K 45/06* (2006.01)
*A61P 1/04* (2006.01)

(52) U.S. Cl.
CPC ........ *A61K 31/7072* (2013.01); *A61K 31/519* (2013.01); *A61K 45/06* (2013.01); *A61P 1/04* (2018.01)

(58) Field of Classification Search
CPC .............. A61K 31/7072; A61K 31/513; A61K 2300/00; A61P 1/04; A61P 35/00
See application file for complete search history.

(56) References Cited

U.S. PATENT DOCUMENTS

| | | |
|---|---|---|
| 5,296,216 A | 3/1994 | Turner |
| 5,470,838 A | 11/1995 | von Borstel et al. |
| 5,736,531 A | 4/1998 | von Borstel et al. |
| 5,968,914 A | 10/1999 | von Borstel et al. |
| 6,090,932 A | 7/2000 | McGee et al. |
| 6,232,298 B1 | 5/2001 | von Borstel et al. |
| 6,344,447 B2 | 2/2002 | von Borstel et al. |
| 6,992,072 B2 | 1/2006 | Walker |
| 7,166,581 B1 | 1/2007 | von Borstel et al. |
| 7,709,459 B2 | 5/2010 | von Borstel et al. |
| 7,776,838 B1 | 8/2010 | von Borstel et al. |
| 7,998,967 B2 | 8/2011 | Garland et al. |
| 8,853,227 B2 | 10/2014 | Garland et al. |
| 9,382,287 B2 * | 7/2016 | Garland ............. A61K 45/06 |
| 9,700,547 B2 | 7/2017 | Basso et al. |
| RE48,253 E * | 10/2020 | Garland ............. A61P 29/00 |
| 2004/0029823 A1 | 2/2004 | McKay et al. |
| 2009/0325969 A1 | 12/2009 | Garland et al. |
| 2011/0319419 A1 | 12/2011 | Garland et al. |
| 2012/0029071 A1 | 2/2012 | Biswal et al. |
| 2012/0294869 A1 | 11/2012 | Pizzorno et al. |
| 2015/0072945 A1 | 3/2015 | Garland et al. |
| 2016/0193354 A1 | 7/2016 | Noe et al. |
| 2020/0397790 A1 | 12/2020 | Garland et al. |
| 2021/0236530 A1 | 8/2021 | Garland et al. |
| 2022/0008422 A1 | 1/2022 | Garland et al. |

FOREIGN PATENT DOCUMENTS

| | | |
|---|---|---|
| EP | 0801062 A1 | 10/1997 |
| JP | H06508846 A | 10/1994 |
| JP | H10511689 A | 11/1998 |
| WO | WO9301202 A1 | 1/1993 |
| WO | WO9426761 A1 | 11/1994 |
| WO | WO9601115 A1 | 1/1996 |
| WO | WO03099297 A1 | 12/2003 |
| WO | WO2005020885 A2 | 3/2005 |
| WO | WO2005026186 A1 | 3/2005 |
| WO | WO2008083465 A1 | 7/2008 |
| WO | WO2009114325 A2 | 9/2009 |
| WO | WO2020036982 A1 | 2/2020 |

OTHER PUBLICATIONS

Saif et al., Cancer Chemother. Pharmacol., 2006, 58, p. 136-142. (Year: 2006).*
Roberts et al., Nature Communications, 2018, 9, article No. 4073, 10 pages, Published: Oct. 4, 2018. (Year: 2018).*
Seiter et al., Cancer, 1993, 71(5), p. 1875-1881. (Year: 1993).*
Ilgo et al., Differential effects of 2,2'-anhydro-5-ethyluridine, a uridine phosphorylase inhibitor, on the antitumor activity of 5-fluorouridine and 5-fluoro-2'-deoxyuridine, Biochemical Pharmacology, Apr. 1990, vol. 39, No. 7, p. 1247-1253.
Grancharov et al., Inhibition of uridine phosphorylase by some pyrimidine derivatives, Biochemical Pharmacology, Jun. 1991, vol. 41, No. 11, p. 1769-1772, abstract only.
Igo et al., In vivo Antitumor Effects of Fluoropyrimidines on Colon Adenocarcinoma 38 and Enhancement by Leucovorin, Japanese Journal of Cancer Research, Apr. 1992, vol. 83, p. 392-396.
Mironova et al., Prospects for the use of regulators of oxidative stress in the comprehensive treatment of the novel Coronavirus Disease 2019 (COVID-19) and its complications, European Review for Medical and Pharmacological Sciences, 2020, vol. 24, p. 8585-8591.

(Continued)

*Primary Examiner* — Jonathan S Lau
(74) *Attorney, Agent, or Firm* — Darya C. Cheng; Bret E. Field; Bozicevic, Field & Francis LLP

(57) ABSTRACT

Methods for treating a subject for mucositis are provided. Aspects of the methods include administering an effective amount of a cancer therapy toxicity-reducing adjuvant in combination with uridine or a prodrug thereof to the subject. In certain embodiments, the cancer therapy toxicity-reducing adjuvant is a 2,2'-anhydropyrimidine, or a derivative thereof. Also provided are compositions for use in practicing the subject methods. The subject methods and compositions find use in a variety of different cancer therapy applications.

20 Claims, 19 Drawing Sheets

(56) References Cited

OTHER PUBLICATIONS

Mosentsov et al., Does the Operation of Mitochondrial ATP-Dependent Potassium Channels Affect the Structural Component of Mitochondrial and Endothelial Dysfunctions in Experimental Parkinsonism?, Bulletin of Experimental Biology and Medicine, Feb. 2021, vol. 170, No. 4, p. 431-435.

Veres et al., Inhibition of uridine phosphorylase by pyrimidine nucleoside analogs and consideration of substrate binding to the enzyme based on solution conformation as seen by NMR spectroscopy, Eur. J. Biochem., Aug. 1988, vol. 178, p. 173-181.

Ashour et al., 5-(m-Benzyloxybenzyl)barbituric acid acyclonucleoside, a uridine phosphorylase inhibitor, and 2',3',5'- tri-O-acetyluridine, a prodrug of uridine, as modulators of plasma uridine concentration. Implications for chemotherapy, Biochem Pharmacol (1996), 51(12):1601-1611.

Ashour et al., Effect of 5-(phenylselenenyl)acyclouridine, an inhibitor of uridine phosphorylase, on plasma concentration of uridine released from 2',3',5'-tri-O-acetyluridine, a prodrug of uridine: relevance to uridine rescue in chemotherapy, Cancer Chemother Pharmacol (2000), 46(3):235-240.

Ashour et al., Modulation of 5-fluorouracil host toxicity by 5-(benzyloxybenzyl)barbituric acid acyclonucleoside, a uridine phosphorylase inhibitor, and 2',3',5'-tri-O-acetyluridine, a prodrug of uridine, Biochem Pharmacol (2000), 60(3):427-431.

Brunetti et al., 5-Fluorouracil enhances azidothymidine cytotoxicity: in vitro, in vivo, and biochemical studies, Cancer Res (1990), 50(13):4026-4031.

Christensen et al., Effect of hydration on methotrexate plasma concentrations in children with acute lymphocytic leukemia, J Clin Oncology (1988), 6(5):797-801.

Darnowski et al., Fluorouracil plus azidothymidine cytotoxicity in vitro: Relationship to cellular thymidine kinase activity, Proc of American Assoc for Cancer Research (1990), 31:398.

Darnowski et al., Resistance to Azido-Thymidine Cytotoxicity in the Human Colon Tumor Cell Line HCT15 is Associated with Enhanced Removal of AZT from Cellular DNA, Proc of American Assoc for Cancer Research (1991), 32:358.

Drabikowska et al., Inhibitor properties of some 5-substituted uracil acyclonucleosides, and 2,2'-anhydrouridines versus uridine phosphorylase from *E. coli* and mammalian sources, Biochem Pharmacol (1987), 36(23):4125-4128.

Ettmayer et al., Lessons learned from marketed and investigational prodrugs, Medicinal Chemistry (2004), 47(10):2393-2404.

Howell et al., Cytokinetic comparison of thymidine and leucovorin rescue of marrow in humans after exposure to high-dose methotrexate, Cancer Res (1979), 39(4):1315-1320.

Howell et al., Thymidine Rescue of High-Dose Methotrexate in Humans, Cancer Res (1978), 38(2): 325-330.

Martin et al., High-dose 5-fluorouracil with delayed uridine "rescue" in mice, Cancer Res (1982), 42(10):3964-3970.

Martin et al., Use of oral uridine as a substitute for parenteral uridine rescue of 5-fluorouracil therapy, with and without the uridine phosphorylase inhibitor 5-benzylacyclouridine, Cancer Chemother Pharmacol (1989), 24(1):9-14.

Mazokopakis et al., Wild chamomile (*Matricaria recutita* L.) mouthwashes in methotrexate-induced oral mucositis, Phytomedicine (2005), 12(1-2):25-27.

Morissette et al., High-throughput crystallization: polypmorphs, salts, co-crystals and solvates of pharmaceutical solids, Adv Drug Deliv Rev (2004), 56(3):275-300.

Newman et al., Increased Sensitivity to Azidothymidine in a Subline of CCRF-CEM Human Leukemia Cells Resistant to Methotrexate, Proceedings of the American Assoc. for Cancer Research (1991), 32:413.

Pizzorno et al., Phase I clinical and pharmacological studies of benzylacyclouridine, a uridine phosphorylase Inhibitor, Clin Cancer Res (1998), 4(5):1165-1175.

Scanlon et al., Overexpression of DNA replication and repair enzymes in cisplatin-resistant human colon carcinoma HCT8 cells and circumvention by azidothymidine, Cancer Commun (1989), 1(4):269-275.

Semon et al., Potentiation of the Antitumor Activity of Methotrexate by Concurrent Infusion of Thymidine, Cancer Res (1978), 38:2905-2911.

Stella, Prodrugs as therapeutics, Expert Opinion on Therapeutic Patents (2004), 14,(3):277-280.

Sterba et al., High-dose methotrexate and/or leucovorin rescue for the treatment of children with lymphoblastic malignancies: do we really know why, when and how?, Neoplasma (2005), 52 6):456-463.

Tattersall et al., The reversal of methotrexate toxicity by thymidine with maintenance of antitumour effects, Nature (1975), 253 (5488):198-200.

Testa, Prodrug research: futile or fertile?, Biochemical Pharmacology (2004), 68(11):2097-2106.

Tosi et al., Azidothymidine-induced cytotoxicity and incorporation into DNA in the human colon tumor cell line HCT-8 Is enhanced by methotrexate in vitro and in vivo, Cancer Res (1992), 52(15):4069-4073.

Veres et al., 5-Substituted-2,2'-anhydrouridines, potent inhibitors of uridine phosphorylase, Biochem Pharmacol (1985), 34(10):1737-1740.

Vippagunta et al. Crystalline solids, Adv Drug Deliv Rev (2001), 48(1):3-26.

Weber et al., Azidothymidine inhibition of thymidine kinase and synergistic cytotoxicity with methotrexate and 5-fluorouracil in rat hepatoma and human colon cancer cells, Cancer Commun (1990), 2(4):129-133.

Weber et al., AZT: a biochemical response modifier of methotrexate and 5-fluorouracil cytotoxicity in human ovarian and pancreatic carcinoma cells, Cancer Commun (1991), 3(4):127-132.

Weber et al., Regulation of de novo and salvage pathways in chemotherapy, Adv Enzyme Regul (1991), 31:45-67.

Wolff, Burger's Medicinal Chemistry and Drug Discovery, 5th edition (1994), vol. 1, pp. 975-977.

Leyva et al., Phase I and Pharmacokinetic Studies of High-Dose Uridine Intended for Rescue from 5-Fluorouracil Toxicity, Cancer Research, Dec. 1984, vol. 44, p. 5928-5933.

Maria et al., Radiation-Induced Oral Mucositis, Frontiers in Oncology, May 2017, vol. 7, Art. 89, p. 1-23.

Renck et al., Human uridine phosphorylase-1 inhibitors: a new approach to ameliorate 5-fluorouracil-induced intestinal mucositis, Invest New Drugs, Jul. 2014, vol. 32, p. 1301-1307.

Al Safarjalani et al., 5-(Phenylthio)acyclouridine: a powerful enhancer of oral uridine bioavailability: relevance to chemotherapy with 5-fluorouracil and other uridine rescue regiments, Cancer Chemother Pharmacol, Feb. 2005, vol. 55, p. 541-551.

Veres et al., The effect of the 3'-OH group on the conformation and binding ability of anhydropyrimidine nucleosides to uridine phosphorylase, Archives of Biochemistry and Biophysics, vol. 286, No. 1, Apr. 1991, p. 1-5, abstract only.

Le et al., Uridine Prevents Fenofibrate-Induced Fatty Liver, PLoS One, Jan. 2014, vol. 9, No. 1, p. 1-14.

Cicko et al., Uridine supplementation exerts anti-inflammatory and anti-fibrotic effects in an animal model of pulmonary fibrosis, Respiratory Research, 2015, vol. 16, No. 105, p. 1-10.

Labbe et al., Drug-induced liver injury through mitochondrial dysfunction: mechanisms and detection during preclinical safety studies, Fundamental & Clinical Pharmacology, Aug. 2008, vol. 22, No. 4, p. 335-353.

Da Silva et al., Therapeutic effect of uridine phosphorylase 1 (UPP1) inhibitor on liver fibrosis in vitro and in vivo, European Journal of Pharmacology, Jan. 2021, vol. 890, No. 173670, p. 1-11.

Golovinski et al., Antiviral, Antibacterial and Antitumor Activity of the Hydrazide and the Ethyl Ester of 2,2'-Anhydro-I-(p-D-arabinofuranosyl)-orotic Acid, Arzneim.-Forsch. Drug Res. 30 (II), Nr. 12 (1980), p. 2087-2090.

PubChem CID 73805817, May 29, 2014, Retrieved from the Internet on May 4, 2022, URL: https://pubchem.ncbi.nlm.nih.gov/compound/73805817, 8 pages.

(56) References Cited

OTHER PUBLICATIONS

Tang et al., Inhibition of Autotaxin with GLPG1690 Increases the Efficacy of Radiotherapy and Chemotherapy in a Mouse Model of Breast Cancer, Molecular Cancer Therapeutics, Sep. 23, 2019, p. 1-13.
Connolly et al., Uridine and its nucleotides: biological actions, therapeutic potentials, Trends Pharmacol Sci, May 1999, vol. 20, No. 5, p. 218-225.
Melichar et al., Intestinal permeability in patients with chemotherapy-induced stomatitis, J Cancer Res Clin Oncol, May 2001, vol. 127, No. 5, p. 314-318.
Sonis et al., Phase II investigational oral drugs for the treatment of radio/chemotherapy induced oral mucositis, Expert Opinion on Investigational Drugs, Jan. 2018, vol. 27, No. 2, p. 147-154.
Yuan et al., Emerging therapies for the prevention and treatment of oral mucositis, Expert Opinion on Emerging Drugs, Aug. 2014, vol. 19, No. 3, p. 343-351.
Zidan et al., Multidrug Chemotherapy Using Bleomycin, Methotrexate, and Cisplatin Combined with Radical Radiotherapy in Advanced Head and Neck Cancer, Cancer, Jan. 1987, vol. 59, No. 1, p. 24-26.
Shannahoff et al., 2,2'-Anhydropyrimidine nucleosides. Novel syntheses and reactions, J. Org. Chem., Feb. 1973, vol. 38, No. 3, p. 593-598.
Gupta et al., A randomised clinical trial to contrast radiotherapy with radiotherapy and methotrexate given synchronously in head and neck cancer, Clinical Radiology, 1987, vol. 38, p. 575-581.

\* cited by examiner

METHODS AND COMPOSITIONS FOR TREATING MUCOSITIS

CROSS-REFERENCE TO RELATED APPLICATIONS

This application is a continuation in part application of International Application Serial No. PCT/US2019/046386 filed Aug. 13, 2019, which application, pursuant to 35 U.S.C. § 119 (e), claims priority to the filing date of U.S. Provisional Patent Application Ser. No. 62/718,831 filed Aug. 14, 2018; the disclosure of which application is herein incorporated by reference.

INTRODUCTION

Mucositis is a condition that often results as a complication of chemotherapy and/or radiation therapy for cancer. (Pulito et al., "Oral Mucositis: The Hidden Side of Cancer Therapy," J Exp Clin Cancer Res. (2020) 39:210; Lalla et al., "Oral Mucositis Due to High-Dose Chemotherapy and/or Head and Neck Radiation Therapy," J Natl Cancer Inst Monogr. (2019) 53; Sonis et al., "Mucositis Study Section of the MASCC and the ISOO; Perspectives on cancer therapy-induced mucosal injury: pathogenesis, measurement, epidemiology, and consequences for patients," Cancer (2004) 100 (9 Suppl): 1995-2025). Mucositis is a condition characterized by swelling, irritation, and distress of mucosal linings such as those of the alimentary and gastrointestinal tract, including oral and oral pharyngeal cavities, as well as of the nasal, optical, vaginal and rectal mucosa. (Van Sebille et al., "Management of Mucositis During Chemotherapy: From Pathophysiology to Pragmatic Therapeutics," Curr Oncol Rep. (2015) (11):50). Mucositis can result in mouth and throat sores, diarrhea, abdominal cramping and tenderness, and rectal ulcerations. (Van Sebille et al., "Management of Mucositis During Chemotherapy: From Pathophysiology to Pragmatic Therapeutics," Curr Oncol Rep. (2015) 17(11): 50; Davy et al., "Systematic review of interventions to mitigate radiotherapy-induced oral mucositis in head and neck cancer patients," Support Care Cancer. (2020)). The inflammation of mucous membranes often involves infection and/or ulceration. Mucositis is a serious and often very painful disorder. (Lalla et al., "Chemotherapy or radiation-induced oral mucositis," Dent Clin North Am. (2014) 58(2): 341-9). Exposure to radiation often results in significant disruption of cellular integrity in mucosal epithelium and the underlying connective tissue, leading to inflammation, infection and/or ulceration at mucosal sites such as, for example, in the mouth, throat and other portions of the gastrointestinal (GI) tract. (Thomsen et al., "Adjunctive Treatments for the Prevention of Chemotherapy- and Radiotherapy-Induced Mucositis," Integr Cancer Ther. (2018) 17(4):1027-1047).

Mucositis adversely impacts the quality of life of cancer patients in several ways. (Kim et al., "Association of oral mucositis with quality of life and symptom clusters in patients with solid tumors receiving chemotherapy," Support Care Cancer. (2012) 20(2): 395-403; Cheng et al., "Oral mucositis in pediatric and adolescent patients undergoing chemotherapy: the impact of symptoms on quality of life," Support Care Cancer. (2012) 20(10): 2335-42). Patients may experience intense pain, nausea and gastro-enteritis. The mouth and throat sores of mucositis can cause significant pain and make it difficult to eat, drink, and even take oral medication. In general, symptoms of mucositis appear within three to ten days after the start of cancer treatment and can last several weeks after cessation of treatment. (Sonis et al., "Oral complications of cancer therapy," Oncology (Williston Park) (2002) 16(5):680-6).

The incidence of mucositis, as well as its severity, depends on factors such as the type and duration of the cancer treatment. Mucositis affects 40-100 percent of patients receiving higher doses of chemotherapy. (Chen et al., "Oral Mucositis: An Update on Innate Immunity and New Interventional Targets," J Dent Res. (2020) 99(10): 1122-1130; Trotti et al., "Mucositis incidence, severity and associated outcomes in patients with head and neck cancer receiving radiotherapy with or without chemotherapy: a systematic literature review," Radiother Oncol. (2003) 66(3):253-62; Maria et al., "Radiation-Induced Oral Mucositis," Front Oncol. (2017) 7:89). Mucositis afflicts over 400,000 patients a year in the US, and the incidence is growing as the need for radiation and chemotherapy treatments grows. (Posner et al., "Novel agents for the treatment of mucositis," J Support Oncol. (2007) 5 (9 Suppl 4):33-9). The severity of mucositis can limit subsequent doses of chemotherapy. (Cinausero et al., "New Frontiers in the Pathobiology and Treatment of Cancer Regimen-Related Mucosal Injury," Front Pharmacol. (2017) 8:354).

Efforts to counter the discomforts of mucositis can lead to disruptions in cancer treatment, alterations in treatment dosages, or shifting to different modes of treatment. Severe mucositis can also lead to the need for parenteral nutrition or hospitalization, as intravenous feeding due to mouth ulcers, cramps, extreme pain, gut denuding and severe diarrhea. Thus, the development of effective approaches to preventing and treating mucositis is important for improving the care of cancer patients.

Oral mucositis is an example of a specific type of mucositis. Oral mucositis is an acute, painful, costly, and sometimes debilitating complication of some cancer therapies. (Duncan et al., "Oral and intestinal mucositis—causes and possible treatments," Aliment Pharmacol Ther. (2003) 18(9):853-74). Oral mucositis is prevalent in patient populations with head and neck malignancies being treated with chemotherapy and/or radiation. (Oronsky et al., "A Review of Clinical Radioprotection and Chemoprotection for Oral Mucositis," Transl Oncol. (2018) 11(3):771-778). The oral cavity is lined with mucosal epithelium, and exposure to chemotherapeutics results in the disruption of cellular integrity leading to the development of ulcerative lesions. The mucositis can be mild, requiring little intervention, to severe (hypovolemia, electrolyte abnormalities, and malnutrition) that can result in fatal complications. This condition affects a significant fraction of cancer patients world-wide.

The onset of oral mucositis usually involves a four-phase process. (Sonis, "Mucositis as a biological process: a new hypothesis for the development of chemotherapy-induced stomatotoxicity," Oral Oncol. (1998) 34(1): 39-43). The primary phase is inflammatory/vascular in nature, marked by cytokine release from the epithelium brought on by damage caused by radiation and/or chemotherapy. The second phase, referred to as the epithelial phase, is signaled by atrophy and ulceration of the mucosal epithelium. The third phase is defined as the ulcerative/bacterial phase, represented by ulcerative lesions that are prone to bacterial infection, further compromising the patients' immune system. These painful lesions often limit a patient's ability to eat and drink and, in some cases, require hospitalization. The presence of these lesions can also interrupt scheduled chemotherapy treatments. The last phase, the healing phase, is characterized by a proliferation and differentiation of epithelium as well as bacterial control.

Mucositis patients are highly susceptible to infection, as a breach in the otherwise protective linings of the oral mucosa and gastrointestinal tract can have serious consequences. (Bertolini et al., "*Candida albicans* induces mucosal bacterial dysbiosis that promotes invasive infection," PLOS Pathog. (2019) 15(4):e1007717). The alimentary canal and GI tract are colonized by a vast array of microorganisms, and mucosal lesions can serve as portals of entry for endogenous microorganisms, becoming sites of secondary infection. (Sabeti Aghabozorgi et al., "Molecular determinants of response to 5-fluorouracil-based chemotherapy in colorectal cancer: The undisputable role of micro-ribonucleic acids," World J Gastrointest Oncol. (2020) 12(9): 942-956).

The clearance of uridine is controlled by UPase, and the inhibition of UPase leads to an increase in uridine (1 uridine salvage). Administration of TK-90 increases systemic uridine. Increased systemic uridine is associated with protection from drug-induced toxicity in many situations. (Cicko et al., "Uridine supplementation exerts anti-inflammatory and anti-fibrotic effects in an animal model of pulmonary fibrosis," Respir Res. (2015) 16(1):105; Wang et al., "Uridine treatment protects against neonatal brain damage and long-term cognitive deficits caused by hyperoxia," Brain Res. (2018) 1688:47-53; Goren et al., "Neuroprotective effects of uridine in a rat model of neonatal hypoxic-ischemic encephalopathy," Neurosci Lett. (2013) 542:65-70; Wang et al., "Uridine treatment protects against neonatal brain damage and long-term cognitive deficits caused by hyperoxia," Brain Res. (2018) 1688:47-53). However, uridine itself is not a realistic drug candidate. The extremely short elimination $t_{1/2}$ of uridine makes its use problematic. Uridine is essentially cleared in a single pass of blood through the liver, primarily by UPase, and is replaced in a highly regulated manner by new uridine formed by de novo synthesis. (Gasser et al., "Novel single pass exchange of circulating uridine in rat liver," Science (1981) 213: 777-778). In addition, oral administration of uridine is associated with considerable GI dysfunction. (van Groeningen et al., "Clinical and pharmacologic study of orally administered uridine," J Natl Cancer Inst. (1991) 83: 437-41).

SUMMARY

Methods for treating a subject for mucositis are provided. Aspects of the methods include administering an effective amount of a cancer therapy toxicity-reducing adjuvant in combination with a uridine plasma level modulator, e.g., uridine or a prodrug thereof, to the subject. In certain embodiments, the cancer therapy toxicity-reducing adjuvant is a 2,2'-anhydropyrimidine, or a derivative thereof. Also provided are compositions for use in practicing the subject methods. The subject methods and compositions find use in a variety of different cancer therapy applications.

DEFINITIONS

Figure 1:
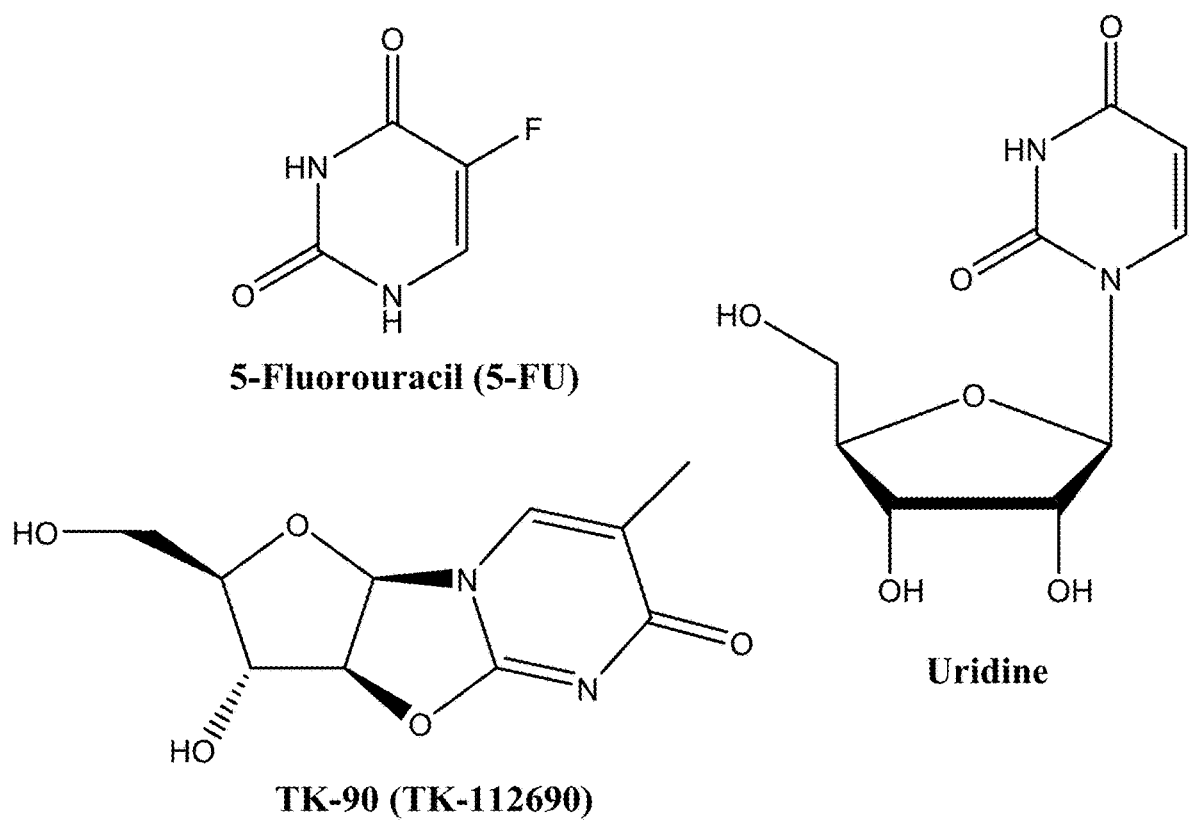
FIG. 1 depicts the chemical structures of 5-FU, TK-90, and uridine.

When describing the compounds, pharmaceutical compositions containing such compounds, and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

"Acyl" refers to a radical —C(O)R, where R is hydrogen, alkyl, cycloalkyl, heterocycloalkyl, aryl, arylalkyl, heteroalkyl, or heteroaryl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, heterocycloalkyl, aryl, arylalkyl, heteroalkyl, heteroaryl, heteroarylalkyl and R is hydrogen, alkyl, alkoxy, cycloalkyl, heterocycloalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)H, —OC(O)-alkyl, —OC(O)-aryl or —OC(O)— cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkynyl and alkynylene. Aliphatic groups typically have from 1 or 2 to 6 or 12 carbon atoms.

"Alkenyl" refers to monovalent olefinically unsaturated hydrocarbyl groups having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkoxy" refers to the group —O-alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Alkoxycarbonylamino" refers to the group —NRC(O)OR' where R is hydrogen, alkyl, aryl or cycloalkyl, and R' is alkyl or cycloalkyl.

"Alkyl" refers to monovalent saturated aliphatic hydrocarbyl groups particularly having up to about 12 or 18 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "alkyl" also includes "cycloalkyls" as defined herein.

"Alkylene" refers to divalent saturated aliphatic hydrocarbyl groups particularly having up to about 12 or 18 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$) CH$_2$—) and the like.

"Alkynyl" refers to acetylenically unsaturated hydrocarbyl groups particularly having up to about 12 or 18 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Amino" refers to the radical —NH$_2$.

"Amino acid" refers to any of the naturally occurring amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

"Aminocarbonyl" refers to the group C(O)NRR where each R is independently hydrogen, alkyl, aryl or cycloalkyl, or where the R groups are joined to form an alkylene group.

"Aminocarbonylamino" refers to the group —NRC(O) NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalky, or where the R groups are joined to form an alkylene group.

"Amino-containing saccharide group" refers to a saccharide group having an amino substituent. Representative amino-containing saccharide include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like.

"Aralkyl" or "arylalkyl" refers to an alkyl group, as defined above, substituted with one or more aryl groups, as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Aryloxy" refers to —O-aryl groups wherein "aryl" is as defined herein.

"Autoimmune disease" or "autoimmune condition" refers an illness that occurs when the body tissues are attacked by its own immune system. Examples of autoimuune disease or conditions include multiple sclerosis, ankylosing spondylitis, Crohn's disease, arthritis, psoriasis, Behçet's disease and psoriatic arthritis.

Azido" refers to the radical —N$_3$.

BAU refers to 5-benzylacyclouridine b.i.d. refers to twice-a-day.

"Carbohydrate" means a mono-, di-, tri-, or polysaccharide, wherein the polysaccharide can have a molecular weight of up to about 20,000, for example, hydroxypropylmethylcellulose or chitosan. "Carbohydrate" also encompasses oxidized, reduced or substituted saccharide monoradical covalently attached to the anhydropyrimidine (e.g., anhydrothymidine or anhydrouridine), or derivative thereof any atom of the saccharide moiety, e.g., via the aglycone carbon atom. The "mono-, di-, tri-, or polysaccharide" can also include amino-containing saccharide groups. Representative "carbohydrate" include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose-, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. The saccharides can be either in their open, r pyranose or furanose forms.

"Carboxyl" refers to the radical —C(O)OH.

"Cyano" refers to the radical —CN.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Heterocycloalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl.

"Halo" or "halogen" refers to fluoro, chloro, bromo and iodo. Halo groups can be either fluoro or chloro.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocycloalkyl, aryl, e.g., heteroaryl, cycloalkenyl, e.g., heterocycloalkenyl, cycloheteroalkenyl, e.g., heterocycloheteroalkenyl and the like having from 1 to 5, and particularly from 1 to 3 heteroatoms. A heteroatom is any atom other than carbon or hydrogen and is typically, but not exclusively, nitrogen, oxygen, sulfur, phosphorus, boron, chlorine, bromine, or iodine. An unsubstituted heteroatom refers to a pendant heteroatom such as an amine, hydroxyl and thiol. A substituted heteroatom refers to a heteroatom that is other than a pendant heteroatom.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. The heteroaryl group can be a 5-20 membered heteroaryl, or 5-10 membered heteroaryl. Particular heteroaryl groups are those derived from thiophen, pyrrole, benzothiophene, benzofuran, indole, pyridine, quinoline, imidazole, oxazole and pyrazine.

"Hydroxyl" refers to the radical —OH.

i.p. refers to intraperitoneal administration.

"Nitro" refers to the radical —NO$_2$.

OM refers to oral mucositis.

PBS refers to phosphate buffered saline

"Peptide" refers to a polyamino acid containing up to 2, 5, 10, or about 100 amino acid residues.

p.o. refers to oral administration.

"Polypeptide" means polyamino acid containing from about 100 amino acid units to about 1,000 amino acid units, from about 100 amino acid units to about 750 amino acid units, or from about 100 amino acid units to about 500 amino acid units.

q.d refers to once-a day treatment.

s.c. refers to subcutaneous administration.

SD refers to standard deviation

SE refers to standard error.

"Side-effect" means an undesirable adverse consequence of drug administration such as mucositis associated with administration of cancer therapy.

"Stereoisomer" as it relates to a given compound is well understood in the art and refers to another compound having the same molecular formula, wherein the atoms making up the other compound differ in the way they are oriented in space, but wherein the atoms in the other compound are like the atoms in the given compound with respect to which atoms are joined to which other atoms (e.g., an enantiomer, a diastereomer, or a geometric isomer). See for example, Morrison and Boyd, Organic Chemistry, 1983, 4th ed., Allyn and Bacon, Inc., Boston, MA, p. 123.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, aralkyl, azido, carboxyl, cyano, cycloalkyl, substituted cycloalkyl, halogen, hydroxyl, imidate, keto, nitro, thioalkoxy, substituted thioalkoxy, thioaryloxy, thioketo, thiol, alkylthio, (substituted alkyl)thio, arylthio, (substituted aryl)thio, alkyl-S(O)—, aryl-S(O)—, alkyl-S(O)$_2$— and aryl-S(O)$_2$. Typical substituents include, but are not limited to, —X, —R$^8$ (with the proviso that R$^8$ is not hydrogen), —O—, =O, —OR$^8$, —SR$^8$, —S—, =S, —NR$^8$R$^9$, =NR$^8$, —CX$_3$, —CF$_3$, —CN, —OCN, —SCN, —NO, —NO$_2$, =N$_2$, —N$_3$, —S(O)$_{2O}$, —S(O)$_2$OH, —S(O)$_2$R$^8$, —OS(O$_2$)O—, —OS(O)$_2$R$^8$, —P(O)(O—)$_2$, —P(O)(OR$^8$)(O—), —OP(O)(OR$^8$)(OR$^9$), —C(O)R$^8$, —C(S)R$^8$, —C(O)OR$^8$, —C(O)NR$^8$R$^9$, —C(O)O, —C(S)OR$^8$, —NR$^{10}$C(O)NR$^8$R$^9$, —NR$^{10}$C(S)NR$^8$R$^9$, —NR$^{11}$C(NR$^{10}$)NR$^8$R$^9$ and —C(NR$^{10}$)NR$^8$R$^9$, where each X is independently a halogen.

"Substituted amino" includes those groups recited in the definition of "substituted" herein, and particularly refers to the group N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group.

"Thioalkoxy" refers to the group —S-alkyl.

"Thioaryloxy" refers to the group —S-aryl.

"Thioketo" refers to the group =S.

"Thiol" refers to the group —SH.

TK-90 is an authentic uridine phosphorylase (UPase) (Cao et al., "Uridine phosophorylase: an important enzyme in pyrimidine metabolism and fluoropyrimidine activation," Drugs Today (Barc). (2004) 40:431-43; Pizzorno et al., "Homeostatic control of uridine and the role of uridine phosphorylase: a biological and clinical update," Biochim Biophys Acta. (2002) 1587(2-3):133-44) inhibitor that has successfully completed its third clinical trial as a mitigator of methotrexate-induced mucositis. TK-90 has no known side effects, has proven efficacy as an agent to mitigate chemotherapy-induced mucositis, is readily synthesized, and is active when dosed parenterally or orally. 5-flurouracil (5-FU) is an anti-cancer therapy widely used to treat colon cancer. Approximately 80% of the patients who receive 5-FU for their disease develop mucositis. (Kuchay, "A review of complementary therapies for chemotherapy induced gastrointestinal mucositis," Drug Discov Ther. (2017) 10(6): 292-299). A UPase inhibitor structurally very different from TK-90 is reported to protect from 5-FU-induced mucositis. (Renck et al., "Human uridine phosphorylase-1 inhibitors: a new approach to ameliorate 5-fluorouracil-induced intestinal mucositis," Invest New Drugs (2014) 32(6):1301-7).

"Uridine phosphorylase" refers in enzymology to a phosphorylase (EC 2.4.2.3) that catalyzes the chemical reaction: uridine+phosphate→uracil+alpha-D-ribose 1-phosphate. The two substrates of this enzyme are uridine and phosphate, whereas its two products are uracil and alpha-D-ribose 1-phosphate. This enzyme belongs to the family of glycosyltransferases, specifically the pentosyltransferases. The systematic name of this enzyme class is uridine: phosphate alpha-D-ribosyltransferase. Other names in common use include pyrimidine phosphorylase, UrdPase, UPH, and UPase. This enzyme participates in pyrimidine metabolism.

"Uridine Supplement" refers to either a formulated product containing uridine or a formulated product containing a uridine precursor such as uridine monophosphate or acetylated uridine that converts to uridine in the body. The formulated product could be a solution, a capsule, a tablet, or a cream. The product could be administered po, ip, sc, or iv. The uridine supplement could be administered as part of a more complex mixture such as a nutritional supplement.

One having ordinary skill in the art will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

DETAILED DESCRIPTION

Methods for treating a subject for mucositis are provided. Aspects of the methods include administering an effective amount of a cancer therapy toxicity-reducing adjuvant in combination with a uridine plasma level modulator to the subject. In certain embodiments, the cancer therapy toxicity-reducing adjuvant is a 2,2'-anhydropyrimidine or a derivative thereof. Also provided are compositions for use in practicing the subject methods. The subject methods and compositions find use in a variety of different cancer therapy applications.

In some instances, anhydronucleosides are employed in combination with a uridine plasma level modulator to ameliorate the toxic side-effects of cancer therapy. Anhydronucleosides are analogs of natural nucleosides, often finding use as intermediates in the synthesis of nucleoside derivatives. They are characterized by having, in addition to the N-glycoside linkage, a covalent linkage either directly or via bridging atoms between the 2', 3', or 5' carbons of the sugar and a carbon, oxygen or nitrogen atom (other than the nitrogen of the glycoside bond) of the base. The anhydropyrimidines are characterized by a pyrimidine base that is covalently linked either directly or via bridging atoms between the 2', 3', or 5' carbons of the sugar and a carbon, oxygen or nitrogen atom (other than the nitrogen of the glycoside bond) of the pyrimidine base. In some instances, the adjuvant employed with a uridine plasma level modulator is 2,2'-anhydropyrimidine or a derivative thereof.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

While the method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

In further describing the subject invention, the subject methods are described first in greater detail, followed by a review of the various compositions, e.g., formulations and kits, that may find use in the subject methods, as well as a discussion of various representative applications in which the subject methods and compositions find use.

Methods

As summarized above, methods of treating a subject for mucositis are provided. An aspect of the subject methods is that a cancer therapy toxicity-reducing adjuvant is administered to the subject in combination with a uridine plasma level modulator, e.g., uridine or a prodrug thereof. In certain embodiments, the cancer therapy toxicity-reducing adjuvant (which may also be referred to herein as a uridine maximizing adjuvant) is a 2,2'-anhydropyrimidine, such as a 2,2'-anhydrouridine or analogue/derivative thereof. By "in combination with", is meant that an amount of the cancer therapy toxicity-reducing adjuvant is administered anywhere from simultaneously to up to 5 hours or more, e.g., 10 hours, 15 hours, 20 hours or more, prior to, or after, the uridine plasma level modulator. In certain embodiments, the cancer therapy toxicity-reducing adjuvant and uridine plasma level modulator are administered sequentially, e.g., where the cancer therapy toxicity-reducing adjuvant is administered before or after the uridine plasma level modulator. In yet other embodiments, the cancer therapy toxicity-reducing adjuvant and uridine plasma level modulator are administered simultaneously, e.g., where the cancer therapy toxicity-reducing adjuvant and uridine plasma level modulator are administered at the same time as two separate formulations, or are combined into a single composition, that is administered to the subject. Regardless of whether the cancer therapy toxicity-reducing adjuvant and uridine plasma level modulator are administered sequentially or simultaneously, as illustrated above, or any effective variation thereof, the agents are considered to be administered together or in combination for purposes of the present invention. Routes of administration of the two agents may vary, where representative routes of administration are described in greater detail below.

In the subject methods, an effective amount of a cancer therapy toxicity-reducing active agent is administered to a subject in combination with a uridine plasma level modulator. The phrase "cancer therapy toxicity-reducing adjuvant" refers to an agent that reduces toxicity of a cancer therapy, such as chemotherapy or radiation therapy. Cancer therapy toxicity-reducing adjuvants of interest are those agents that reduce the occurrence and/or intensity of observable toxic side-effects of a given cancer therapy, as observed in the mouse assay described in the Experimental section below, e.g., by 2-fold or more, such as 5-fold or more, including 10-fold or more. Aspects of cancer therapy-reducing adjuvants according to certain embodiments of the invention are that the adjuvants do not substantially reduce, and in certain embodiments have no impact at all, on the effectiveness of the cancer therapy.

The cancer therapy toxicity-reducing adjuvants of interest include 2,2'-anhydropyrimidines and derivatives thereof. In some embodiments, the 2,2'-anhydropyrimidine or derivative thereof is a compound of formula (I):

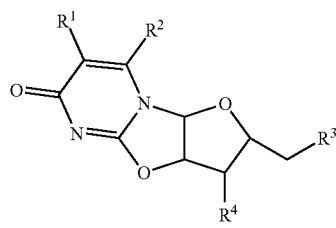

(I)

or the pharmaceutically acceptable salts, solvates, hydrates, and prodrug forms thereof, and stereoisomers thereof,
wherein:
each $R^1$, $R^2$, $R^3$ and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, hydroxyl, halogen, azido, amino, substituted amino, carbohydrate, nucleic acid, amino acid, peptide, dye, fluorophore and polypeptide.

In certain embodiments, the compound is of formula (I), $R^1$, $R^2$, $R^3$ and $R^4$ are independently hydrogen, hydroxyl, heteroatom, $C_1$-$C_{18}$ alkyl, $C_1$-$C_{18}$ substituted alkyl, $C_1$-$C_{18}$ alkenyl, $C_1$-$C_{18}$ acyl, amino, substituted amino, wherein the alkyl, alkenyl or acyl is linear or branched, and optionally substituted with a hydroxyl, an ester and its derivatives, a carboxyl and its derivatives, a cycloalkyl, a heterocycloalkyl, an aryl, a heteroaryl, an aralkyl, a heteroatom, and possibly containing in chain or bridging heteroatoms such as nitrogen, oxygen and sulfur.

Examples of $R^1$ constituents of interest include, but are not limited to: hydrogen; hydroxyl; sulfhydryl; halogen such as fluorine, chlorine, bromine or iodine, as well as pseudohalogen such as a lower alkylsulfonyl group of 1 to 5 carbons such as methyl-, ethyl-, propyl-, isopropyl-, butyl-, isobutyl-, tert-butyl-, and pentasulfonyl or arylsulfonyl such as benzene, p-toluene, p-nitrobenzenesulfonyl groups; lower alkyl containing 1 to 20 carbons such as methyl, ethyl, propyl, isopropyl, butyl, isobutyl, tert-butyl, pentyl and the like, including substituted lower alkyl such as aminomethyl, hydroxymethyl, methoxy, ethyloxy, propyloxy, benzyloxy, imidate, alkylthio, (substituted alkyl)thio, arylthio, (substituted aryl)thio and the like; lower alkenyl containing 1 to 20 carbons such as vinyl and substituted vinyl, ethynyl and substituted ethynyl, where the substituted vinyl or substituted ethynyl designates substitution of the ß position of vinyl or ethynyl by a halogen such as bromine, chlorine, fluorine or iodine, or substitution by an alkyl of 1 to 5 carbon atoms such as methyl, ethyl, propyl, butyl, pentyl and the like, or aralkyl such as benzyl, p-chlorobenzyl, p-nitrobenzyl and the like, or aryl such as phenyl, p-nitrophenyl, p-tolyl, p-anisyl, naphtyl and the like; lower alkanoyl (acyl groups) containing 1 to 20 carbons such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonoyl and the like; lower aryl containing 1 to 20 carbons such as phenyl, p-tolyl, p-chlorophenyl, p-aminophenyl, p-nitrophenyl, p-anisyl and the like; lower aroyl containing 1 to 20 carbons such as benzoyl and naphthoyl, where the aromatic group may be additionally substituted by alkyl, alkoxy, halo, or nitro moieties such as p-toluoyl, p-anisoyl, p-chlorobenzoyl, p-nitrobenzoyl or 2,4-dinitrobenzoyl, pentafluorobenzoyl and the like, or another aroyl such as benzyloxybenzyl and the like; lower aralkyl containing 1 to 20 carbons such as benzyl, benzhydryl, p-chlorobenzyl, m-chlorobenzyl, p-nitrobenzyl, benzyloxybenzyl, pentafluorobenzyl and the like; amino or alkylamino containing 1 to 20 carbons such as a monoalkyl- or monoaralkylamino groups like methylamino, ethylamino, propylamino or benzylamino and the like, dialkylamino such as dimethylamino, diethylamino, dibenzylamino, pyrrolidino, piperidino or morpholino and the like.

Thus, in certain embodiments, $R^1$ is hydrogen, hydroxyl, sulfhydryl, amino, substituted amino, hydroxymethyl, monomethoxy, halogen, pseudohalogen, or a lower hydrocarbon (which hydrocarbon can be substituted or unsubstituted) containing from 1 to 20 atoms. In a particular embodiment, $R^1$ is a lower hydrocarbon selected from alkyl, substituted alkyl, alkenyl, alkanoyl, aryl, aroyl, aralkyl, or alkylamino. In a particular embodiment, $R^1$ is a lower hydrocarbon substituted with alkoxy, substituted alkoxy, imidate, arylthio, or (substituted aryl) thio. In other embodiments, $R^1$ is a lower alkyl selected from methyl, ethyl, propyl, isopropyl, butyl, isobutyl, tert-butyl and pentyl. In other embodiments, $R^1$ is a lower alkenyl selected from vinyl, substituted vinyl, ethynyl, or substituted ethynyl. In other embodiments, $R^1$ is a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonoyl. In other embodiments, $R^1$ is lower aryl selected from phenyl, p-tolyl, p-chlorophenyl, p-aminophenyl, p-nitrophenyl, p-anisyl. In yet other embodiments, $R^1$ is a lower aroyl selected from benzoyl and naphthoyl. In other embodiments, $R^1$ is a lower aralkyl selected from benzyl, benzhydryl, p-chlorobenzyl, m-chlorobenzyl, p-nitrobenzyl, benzyloxybenzyl, or pentafluorobenzyl. In certain other embodiments, $R^1$ is a lower alkylamino is selected from monoalkylamino, monoaralkylamino, dialkylamino, diaralkylamino, and benzylamino.

Compounds of interest include, but are not limited to, those of formula (I) where $R^1$ is selected from hydrogen, fluorine, trifluoromethyl, methyl, ethyl, propyl, butyl, isopropyl, isobutyl, acetyl, propionyl, butyryl, 2-bromovinyl, phenyl, benzyl, benzoyl, benzyloxybenzyl, benzylamino, allyloxyallyl, benzyloxyalkyl, imidatealkyl, arylthio, and (substituted aryl) thio. Thus, in certain embodiments, the compound is of formula (I), and $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH═CH, phenyl, benzyl, benzoyl, benzyloxybenzyl, benzyl-NH—, $CH_3CH_2OCH_2$, benzyl-O—$CH_2$, $CH_3OCH_2$, $CH_3C(NH)$—O—$CH_2$, or $CH_3$-phenyl-O—$CH_2$.

Examples of $R^2$ constituents of interest include, but are not limited to: hydrogen; hydroxyl; sulfhydryl; halogen such as fluorine, chlorine, bromine or iodine, as well as pseudohalogen such as a lower alkylsulfonyl group of 1 to 5 carbons such as methyl-, ethyl-, propyl-, isopropyl-, butyl-, isobutyl-, tert-butyl-, and pentasulfonyl or arylsulfonyl such as benzene, p-toluene, p-nitrobenzenesulfonyl groups; lower alkyl containing 1 to 20 carbons such as methyl, ethyl, propyl, isopropyl, butyl, isobutyl, tert-butyl, pentyl and the like, including substituted lower alkyl such as aminomethyl, hydroxymethyl, methoxy, ethyloxy, propyloxy, and the like; lower alkenyl containing 1 to 20 carbons such as vinyl and substituted vinyl, ethynyl and substituted ethynyl, where the substituted vinyl or substituted ethynyl designates substitution of the ß position of vinyl or ethynyl by a halogen such as bromine, chlorine, fluorine or iodine, or substitution by an alkyl of 1 to 5 carbon atoms such as methyl, ethyl, propyl, butyl, pentyl and the like, or aralkyl such as benzyl, p-chlorobenzyl, p-nitrobenzyl and the like, or aryl such as phenyl, p-nitrophenyl, p-tolyl, p-anisyl, naphtyl and the like; lower alkanoyl (acyl groups) and esters thereof of a main chain containing 1 to 20 carbons such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonoyl and the like; lower aryl containing 1 to 20 carbons such as phenyl, p-tolyl, p-chlorophenyl, p-aminophenyl, p-nitrophenyl, p-anisyl and the like; lower aroyl containing 1 to 20 carbons such as benzoyl and naphthoyl, where the aromatic group may be additionally substituted by alkyl, alkoxy, halo, or nitro moieties such as p-toluoyl, p-anisoyl, p-chlorobenzoyl, p-nitrobenzoyl or 2,4-dinitrobenzoyl, pentafluorobenzoyl and the like, or another aroyl such as benzyloxybenzyl and the like; lower aralkyl containing 1 to 20 carbons such as benzyl, benzhydryl, p-chlorobenzyl, m-chlorobenzyl, p-nitrobenzyl, benzyloxybenzyl, pentafluorobenzyl and the like; lower aryloxy containing 1 to 20 carbons such as phenyloxy (i.e., O-phenyl), benzyloxy (i.e., O-benzyl), benzhydryloxy (i.e., O-benzhydryl), p-chlorobenzyloxy (i.e., O-(p-chlorobenzyl)), m-chlorobenzyloxy (i.e., O-(m-chlorobenzyl)), p-nitrobenzyloxy (i.e., O-(p-nitrobenzyl)), (4-benzyloxybenzyl)-oxy (i.e., O-benzyloxybenzyl), or pentafluorobenzyloxy (i.e., O-pentafluorobenzyl); esters of aryloxys, such as lower aryoloxy (i.e., O-aroyl) containing 1 to 20 carbons such as benzoyloxy (i.e., O-benzoyl), diphenylacetyloxy (i.e., O-diphenylacetyl), p-chlorobenzoyloxy (i.e., O-(p-chlorobenzoyl)), m-chlorobenzoyloxy (i.e., O-(m-chlorobenzoyl)), p-nitrobenzoyloxy (i.e., O-(p-nitrobenzoyl)), (4-benzyloxybenzyl)-oxy (i.e., O-benzyloxybenzyl), or pentafluorobenzyloxy (i.e., O-pentafluorobenzoyl); amino or alkylamino containing 1 to 20 carbons such as a monoalkyl- or monoaralkylamino groups like methylamino, ethylamino, propylamino or benzylamino and the like, dialkylamino such as dimethylamino, diethylamino, dibenzylamino, pyrrolidino, piperidino or morpholino and the like.

Thus, in certain embodiments, $R^2$ is hydrogen, hydroxyl, sulfhydryl, amino, hydroxymethyl, monomethoxy, halogen, pseudohalogen, or a lower hydrocarbon (which hydrocarbon can be substituted or unsubstituted) containing from 1 to 20 atoms, and esters thereof. In a particular embodiment, $R^2$ is a lower hydrocarbon selected from alkyl, alkenyl, alkanoyl, aryl, aroyl, aryloxy, aryoloxy, aralkyl, or alkylamino. In other embodiments, $R^2$ is a lower alkyl selected from methyl, ethyl, propyl, isopropyl, butyl, isobutyl, tert-butyl and pentyl. In other embodiments, $R^2$ is a lower alkenyl selected from vinyl, substituted vinyl, ethynyl, or substituted ethynyl. In other embodiments, $R^2$ is a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonoyl. In other embodiments, $R^2$ is lower aryl selected from phenyl, p-tolyl, p-chlorophenyl, p-aminophenyl, p-nitrophenyl, p-anisyl. In yet other embodiments, $R^2$ is a lower aroyl selected from benzoyl and naphthoyl. In other embodiments, $R^2$ is a lower aralkyl selected from benzyl, benzhydryl, p-chlorobenzyl, m-chlorobenzyl, p-nitrobenzyl, benzyloxybenzyl, or pentafluorobenzyl. In other embodiments, $R^2$ is a lower aryloxy selected from phenyloxy, benzyloxy, benzhydryloxy, p-chlorobenzyloxy, m-chlorobenzyloxy, p-nitrobenzyloxy, (4-benzyloxybenzyl)-oxy, or pentafluorobenzyloxy. In other embodiments, $R^2$ is a lower aryoloxy selected from benzoyloxy, diphenylacetyloxy, p-chlorobenzoyloxy, m-chlorobenzoyloxy, p-nitrobenzoyloxy, (4-benzyloxybenzyl)-oxy, or pentafluorobenzyloxy. In certain other embodiments, $R^2$ is a lower alkylamino is selected from monoalkylamino, monoaralkylamino, dialkylamino, and diaralkylamino. Thus, in certain embodiments, $R^2$ can not only be hydrogen or hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O.

Compounds of interest include, but are not limited to, those of formula (I) where $R^2$ is selected from hydrogen, fluorine, trifluoromethyl, methyl, ethyl, propyl, butyl, isopropyl, isobutyl, acetyl, propionyl, butyryl, 2-bromovinyl, phenyl, phenyloxy, benzyl, benzoyl, benzoyloxy and benzyloxybenzyl. Thus, in certain embodiments, the compound is of formula (I), and $R^2$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH═CH, phenyl, phenyloxy, benzyl, benzoyl, benzoyloxy, or benzyloxybenzyl.

In specific embodiments of interest, the compound is of formula (I), and $R^2$ is hydrogen, hydroxyl, or an O-linked substituent. This includes compounds of formula (I), where $R^2$ is H, OH or $C_6H_5C(O)O$.

Examples of $R^3$ of interest include, but are not limited to: hydrogen; hydroxyl; azido; sulfhydryl; halogen; pseudohalogen; lower alkyl containing 1 to 20 carbons such as methyl, ethyl, propyl, isopropyl, butyl, isobutyl, tert-butyl, pentyl and the like, including a substituted lower alkyl such as aminomethyl, hydroxymethyl, methoxy, ethyloxy, propyloxy, and the like; lower alkanoyl (acyl) including esters thereof of a main chain of 1 to 20 carbon atoms such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonoyl and the like; lower aryl such as phenyl, p-nitrophenyl, p-tolyl, p-anisyl, naphtyl and the like; lower aroyl (acyl radical of an aromatic acid) of 1 to 20 carbons such as benzoyl and naphthoyl, where the aromatic group may be additionally substituted by alkyl, alkoxy, halo, or nitro moieties such as p-toluoyl, p-anisoyl, p-chlorobenzoyl, p-nitrobenzoyl or 2,4-dinitrobenzoyl, pentafluorobenzoyl and the like; lower aryloxy of 1 to 20 carbons such as phenyloxy, benzyloxy, benzhydryloxy, p-chlorobenzyloxy, m-chlorobenzyloxy, p-nitrobenzyloxy, (4-benzyloxybenzyl)-oxy, or pentafluorobenzyloxy and the like; as well as esters of aryloxys, such as lower aryoloxy (O-aroyls) of 1 to 20 carbons such as benzoyloxy, diphenylacetyloxy, p-chlorobenzoyloxy, m-chlorobenzoyloxy, p-nitrobenzoyloxy, (4-benzyloxybenzyl)-oxy, or pentafluorobenzyloxy and the like. $R^3$ may also be adamantyl, or substituted adamantyl.

Thus, in certain embodiments, $R^3$ is hydrogen, hydroxyl, azido, sulfhydryl, hydroxymethyl, halogen, or pseudohalogen. In other embodiments, $R^3$ is a lower hydrocarbon selected from alkyl, alkanoyl, aryl, aroyl, aryloxy, aryoloxy, or aralkyl. In other embodiments, $R^3$ is a lower alkyl selected from methyl, ethyl, propyl, isopropyl, butyl, isobutyl, tert-butyl and pentyl. In other embodiments, $R^3$ is a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonoyl. In other embodiments, $R^3$ is a lower aryl selected from phenyl, p-tolyl, p-chlorophenyl, p-aminophenyl, p-nitrophenyl, p-anisyl and the like. In other embodiments, $R^3$ is a lower aroyl selected from benzoyl and naphthoyl. In yet other certain embodiments, $R^3$ is a lower aralkyl selected from benzyl, benzhydryl, p-chlorobenzyl, m-chlorobenzyl, p-nitrobenzyl, benzyloxybenzyl, or pentafluorobenzyl. In other embodiments, $R^3$ is a lower aryloxy selected from phenyloxy, benzyloxy, benzhydryloxy, p-chlorobenzyloxy, m-chlorobenzyloxy, p-nitrobenzyloxy, (4-benzyloxybenzyl)-oxy, or pentafluorobenzyloxy. In other embodiments, $R^3$ is a lower aryoloxy selected from benzoyloxy, diphenylacetyloxy, p-chlorobenzoyloxy, m-chlorobenzoyloxy, p-nitrobenzoyloxy, (4-benzyloxybenzyl)-oxy, or pentafluorobenzyloxy. Thus, in certain embodiments, $R^3$ can not only be hydrogen or hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O.

Compounds of interest are those of formula (I) where $R^3$ is hydrogen, hydroxyl, halogen, azido, or an O-linked substituent. This includes compounds of formula (I) where $R^3$ is selected from hydrogen, hydroxyl, n-butoxy, isobutyloxy, t-butyloxy, phenyloxy, benzyloxy, benzoyloxy, and pentafluorobenzyloxy. Thus, in certain embodiments, the compound is of formula (I), and $R^3$ is selected from H, OH, $CH_3CH_2CH_2CH_2O$, $(CH_3)_2CH_2CH_2O$, $(CH_3)_3CO$, $C_6H_5O$, benzoyloxy, and pentafluorobenzyloxy.

In specific embodiments of interest, the compound is of formula (I), where $R^3$ is H, OH, F, Cl, Br, I, $N_3$, or $C_6H_5C(O)O$. Of special interest is a compound of formula (I), where $R^3$ is OH, or O-acyl (for example, an ester such as $C_6H_5C(O)O$).

Examples of $R^4$ include but are not limited to hydrogen; hydroxyl; sulfhydryl; halogen such as fluorine, chlorine, bromine or iodine; amino or lower alkylamino. $R^4$ also is exemplified by lower alkyl, with acyl groups which may be lower alkanoyl groups of 1 to 7 carbon atoms such as formyl, acetyl, propionyl, isopropionyl, butyryl, isobutyryl, tert-butyryl and the like, and esters thereof. Thus, $R^4$ can also be aroyl (and esters thereof such as O-linked aroyls, i.e., O-aroyls or aryoloxy) such as benzoyl and naphthoyl wherein the aromatic group may be additionally substituted by alkyl, alkoxy, halo, or nitro moieties such as p-toluoyl, p-anisoyl, p-chlorobenzoyl, p-nitrobenzoyl or 2,4-dinitrobenzoyl and the like. Accordingly, in certain embodiments, $R^4$ can not only be hydrogen or hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O.

Thus, in certain embodiments, $R^4$ is hydrogen; hydroxyl; sulfhydryl; halogen, amino aminomethyl, or amindimethyl. In other embodiments, $R^4$ is a lower alkyl, acyl, aroyl, or aryoloxy. This includes a specific embodiment, where the compound of formula (I) is one where $R^4$ is hydrogen, flourine, hydroxyl, amino, aminomethyl, amindimethyl, t-butyloxy, phenyloxy or benzoyloxy (for example, a compound of formula (I), where $R^4$ is H, F, OH, $NH_2$, $NHCH_3$, $N(CH_3)_2$. $(CH_3)_3CO$, $C_6H_5O$ or $C_6H_5C(O)O$).

Compounds of particular interest are those of formula (I) where $R^4$ is hydrogen, hydroxyl, or an O-linked substituent. In specific embodiments, the compound is of formula (I), where $R^4$ is H, OH or $C_6H_5C(O)O$. Of special interest is a compound of formula (I), where $R^4$ is OH, or O-acyl (for example, an ester such as $C_6H_5C(O)O$).

Of interest are compounds of formula (I) where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzoyl, benzoyloxy, or benzyloxybenzyl, and where $R^3$ and $R^4$ are each hydroxyl. These include the compounds: 2,2'-anhydrouridine; 2,2'-anhydro-5-fluorouridine; 2,2'-anhydro-5-trifluoromethyluridine; 2,2'-anhydro-5-methyluridine; 2,2'-anhydro-5-ethyluridine; 2,2'-anhydro-5-propyluridine; 2,2'-anhydro-5-isopropyluridine; 2,2'-anhydro-5-isobutyluridine; 2,2'-anhydro-5-methylacyluridine; 2,2'-anhydro-5-propylacyluridine; 2,2'-anhydro-5-(2-bromovinyl)-uridine; 2,2'-anhydro-5-phenyluridine; 2,2'-anhydro-5-benzyluridine; 2,2'-anhydro-5-benzoyluridine; and 2,2'-anhydro-5-(benzyloxybenzyl)-uridine. Of special interest is 2,2'-anhydro-5-methyluridine, or the pharmaceutically acceptable salts, solvates, hydrates, and prodrug forms thereof, and stereoisomers thereof.

Additional compounds of interest are compounds of formula (I) where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzyloxy, benzoyl, benzoyloxy, or benzyloxybenzyl, and where $R^3$ is hydroxyl, and $R^4$ is benzoyloxy. These include the compounds: 3'-O-benzoyl-2,2'-anhydrouridine; 3'-O-benzoyl-2,2'-anhydro-5-fluorouridine; 3'-O-benzoyl-2,2'-anhydro-5-trifluoromethyluridine; 3'-O-benzoyl-2,2'-anhydro-5-methyluridine; 3'-O-benzoyl-2,2'-anhydro-5-ethyluridine; 3'-O-benzoyl-2,2'-anhydro-5-propyluridine; 3'-O-benzoyl-2,2'-anhydro-5-isopropyluridine; 3'-O-benzoyl-2,2'-O-anhydro-5-isobutyluridine; 3'-O-benzoyl-2,2'-anhydro-5-methylacyluridine; 3'-O-benzoyl-2,2'-anhydro-5-propylacyluridine; 3'-O-benzoyl-2,2'-anhydro-5-(2-bromovinyl)-uridine; 3'-O-benzoyl-2,2'-anhydro-5-phenylluridine; 3'-O-benzoyl-2,2'-anhydro-5-benzyluridine; 3'-O-benzoyl-2,2'-anhydro-5-benzyoluridine; and 3'-O-benzoyl-2,2'-anhydro-5-(benzyloxybenzyl)-uridine. Of specific interest is 3'-O-benzoyl-2,2'-anhydro-5-methyluridine, or the pharmaceutically acceptable salts, solvates, hydrates, and prodrug forms thereof, and stereoisomers thereof.

Also of interest are compounds of formula (I) where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzyloxy, benzoyl, benzoyloxy, or benzyloxybenzyl, and where $R^3$ is benzoyloxy, and $R^4$ is hydroxyl. These include the compounds: 5'-O-benzoyl-2,2'-anhydrouridine; 5'-O-benzoyl-2,2'-anhydro-5-fluorouridine; 5'-O-benzoyl-2,2'-anhydro-5-trifluoromethyluridine; 5'-O-benzoyl-2,2'-anhydro-5-methyluridine; 5'-O-benzoyl-2,2'-anhydro-5-ethyluridine; 5'-O-benzoyl-2,2'-anhydro-5-propyluridine; 5'-O-benzoyl-2,2'-anhydro-5-isopropyluridine; 5'-O-benzoyl-2,2'-O-anhydro-5-isobutyluridine; 5'-O-benzoyl-2,2'-anhydro-5-methylacyluridine; 5'-O-benzoyl-2,2'-anhydro-5-propylacyluridine; 5'-O-benzoyl-2,2'-anhydro-5-(2-bromovinyl)-uridine; 5'-O-benzoyl-2,2'-anhydro-5-phenylluridine; 5'-O-benzoyl-2,2'-anhydro-5-benzyluridine; 5'-O-benzoyl-2,2'-anhydro-5-benzyoluridine; and 5'-O-benzoyl-2,2'-anhydro-5-(benzyloxybenzyl)-uridine. Of specific interest is 5'-O-benzoyl-2,2'-anhydro-5-methyluridine, or the pharmaceutically acceptable salts, solvates, hydrates, and prodrug forms thereof, and stereoisomers thereof.

The 2,2'-anhydropyrimidine compounds of the invention may be in compositions that contain single stereoisomers, mixtures of stereoisomers, as well various derivatives thereof that can occur as equilibrium mixtures of tautomers. For instance, 2,2'-anhydropyrimidines according to formula (I) include four stereo centers with respect to the furano ring, which includes the α and β anomers, and the L or D mirror image configurations. Examples of stereoisomers of the 2,2'-anhydropyrimidine compounds of the invention are the β-D-isomer, β-L-isomer, α-D-isomer, and α-L-isomer, as well as tautomers and mixtures including a, β-D-isomers, α,β-L-isomers, α-DL-isomers, and β-DL-isomers. Thus, in one embodiment, compositions are provided that consists essentially of a stereoisomer of a 2,2'-anhydropyrimidine that is a β-D-isomer, β-L-isomer, α-D-isomer, or an α-L-isomer. Stereoisomers exhibiting improved activity on a molar basis or improved specificity with respect to interfering with cancer therapy efficacy are of special interest.

Stereoisomers of particular interest include: 2,2'-anhydro-1-(β-D-arabinofuranosyl)uracil; 2,2'-anhydro-1-(β-D-arabinofuranosyl)-5-fluorouracil; 2,2'-anhydro-1-(β-D-arabinofuranosyl)-5-trifluoromethyluracil; 2,2'-anhydro-1-(β-D-arabinofuranosyl)-5-methyluracil; 2,2'-anhydro-1-(β-D-arabinofuranosyl)-5-ethyluracil; 2,2'-anhydro-1-(β-D-arabinofuranosyl)-5-n-propyluracil; 2,2'-anhydro-1-(β-D-arabinofuranosyl)-5-isopropyluracil; 2,2'-anhydro-1-(β-D-arabinofuranosyl)-5-isobutyluracil; 2,2'-anhydro-1-(β-D-arabinofuranosyl)-5-methyacyluracil; 2,2'-anhydro-1-(β-D-arabinofuranosyl)-5-propylacyluracil; 2,2'-anhydro-1-(β-D-arabinofuranosyl)-5-(2-bromovinyl)uracil; 2,2'-anhydro-1-(β-D-arabinofuranosyl)-5-phenyluracil; 2,2'-anhydro-1-(β-D-arabinofuranosyl)-5-benzyluracil; 2,2'-anhydro-1-(β-D-arabinofuranosyl)-5-benzyouracil; and 2,2'-anhydro-1-(β-D-arabinofuranosyl)-5-(3-benzyoxybenzyl)uracil. Further stereoisomers of interest include: 3'-O-benzoyl-2,2'-anhydro-1-(β-D-arabinofuranosyl)uracil; 3'-O-benzoyl-2,2'-anhydro-1-(β-D-arabinofuranosyl)-5-fluoruracil; 3'-O-benzoyl-2,2'-anhydro-1-(β-D-arabinofuranosyl)-5-trifluoromethyluracil; 3'-O-benzoyl-2,2'-anhydro-1-(β-D-arabinofuranosyl)-5-methyluracil; 3'-O-benzoyl-2,2'-anhydro-1-(β-D-arabinofuranosyl)-5-ethyluracil; 3'-O-benzoyl-2,2'-anhydro-1-(β-D-arabinofuranosyl)-5-n-propyluracil; 3'-O-benzoyl-2,2'-anhydro-1-(β-D-arabinofuranosyl)-5-isopropyluracil; 3'-O-benzoyl-2,2'-anhydro-1-(β-D-arabinofuranosyl)-5-isobutyluracil; 3'-O-benzoyl-2,2'-anhydro-1-(β-D-arabinofuranosyl)-5-methyacyluracil; 3'-O-benzoyl-2,2'-anhydro-1-(β-D-arabinofuranosyl)-5-propylacyluracil; 3'-O-benzoyl-2,2'-anhydro-1-(β-D-arabinofuranosyl)-5-(2-bromovinyl)uracil; 3'-O-benzoyl-2,2'-anhydro-1-(β-D-arabinofuranosyl)-5-phenyluracil; 3'-O-benzoyl-2,2'-anhydro-1-(β-D-arabinofuranosyl)-5-benzyluracil; 3'-O-benzoyl-2,2'-anhydro-1-(β-D-arabinofuranosyl)-5-benzyouracil; and 3'-O-benzoyl-2,2'-anhydro-1-(β-D-arabinofuranosyl)-5-(3-benzyoxybenzyl)uracil. Additional stereoisomers of interest include: 5'-O-benzoyl-2,2'-anhydro-1-(β-D-arabinofuranosyl)uracil; 5'-O-benzoyl-2,2'-anhydro-1-(β-D-arabinofuranosyl)-5-fluorouracil; 5'-O-benzoyl-2,2'-anhydro-1-(β-D-arabinofuranosyl)-5-trifluoromethyluracil; 5'-O-benzoyl-2,2'-anhydro-1-(β-D-arabinofuranosyl)-5-methyluracil; 5'-O-benzoyl-2,2'-anhydro-1-(β-D-arabinofuranosyl)-5-ethyluracil; 5'-O-benzoyl-2,2'-anhydro-1-(β-D-arabinofuranosyl)-5-n-propyluracil; 5'-O-benzoyl-2,2'-anhydro-1-(β-D-arabinofuranosyl)-5-isopropyluracil; 5'-O-benzoyl-2,2'-anhydro-1-(β-D-arabinofuranosyl)-5-isobutyluracil; 5'-O-benzoyl-2,2'-anhydro-1-(β-D-arabinofuranosyl)-5-methyacyluracil; 5'-O-benzoyl-2,2'-anhydro-1-(β-D-arabinofuranosyl)-5-propylacyluracil; 5'-O-benzoyl-2,2'-anhydro-1-(β-D-arabinofuranosyl)-5-(2-bromovinyl)uracil; 5'-O-benzoyl-2,2'-anhydro-1-(β-D-arabinofuranosyl)-5-phenyluracil; 5'-O-benzoyl-2,2'-anhydro-1-(β-D-arabinofuranosyl)-5-benzyluracil; 5'-O-benzoyl-2,2'-anhydro-1-(β-D-arabinofuranosyl)-5-benzyouracil; and 5'-O-benzoyl-2,2'-anhydro-1-(β-D-arabinofuranosyl)-5-(3-benzyoxybenzyl)uracil.

Examples of other analogs or derivatives of the 2,2'-anhydropyrimidines of the invention, and stereoisomers thereof include: 3'-O-acetyl-2,2'-anhydro-5-propyluridine (3'-O-acetyl-2,2'-anhydro-1-(β-D-arabinofuranosyl)-5-propyluracil); and 3'-O-acetyl-2,2'-anhydro-5-isopropyluridine (3'-O-acetyl-2,2'-anhydro-1-(β-D-arabinofuranosyl)-5-isopropyluracil); as well as the 2,2'-anhydrocytidines, and analogs and derivatives thereof, of which the stereoisomer 2,2'-anhydro-1-(β-D-arabinofuranosyl)cytosine is one example.

As noted above, stereoisomers and the various 2,2'-anhydropyrimidines of particular interest are those which exhibit improved activity on a molar basis, or improved specificity with respect to not interfering with cancer therapy efficacy. Such compounds can be readily selected for this purpose by comparing against a matrix of compounds of particular interest, such as those illustrated in Table 1 (where the compound is of formula (I)).

TABLE 1

The compound is of formula (I)

| Compound | Stereoisomer | $R^1$ | $R^2$ | $R^3$ | $R^4$ |
|---|---|---|---|---|---|
| I-a | β-D-isomer | H | H | OH | OH |
| I-b | β-D-isomer | $CH_3$ | H | OH | OH |
| I-c | β-D-isomer | $CH_3CH_2$ | H | OH | OH |
| I-d | β-D-isomer | $CH_3CH_2CH$ | H | OH | OH |
| I-e | β-D-isomer | BrCH=CH | H | OH | OH |
| I-f | β-D-isomer | $C_6H_5CH_2$ | H | OH | OH |
| I-g | β-D-isomer | H | H | $C_6H_5C(O)O$ | OH |
| I-h | β-D-isomer | $CH_3$ | H | $C_6H_5C(O)O$ | OH |
| I-i | β-D-isomer | $CH_3CH_2$ | H | $C_6H_5C(O)O$ | OH |
| I-j | β-D-isomer | $CH_3CH_2CH$ | H | $C_6H_5C(O)O$ | OH |
| I-k | β-D-isomer | BrCH=CH | H | $C_6H_5C(O)O$ | OH |
| I-l | β-D-isomer | $C_6H_5CH_2$ | H | $C_6H_5C(O)O$ | OH |
| I-m | β-D-isomer | F—$C_6H_5CH_2$ | H | OH | OH |
| I-n | β-D-isomer | $NO_2$—$C_6H_5CH_2$ | H | OH | OH |
| I-o | β-D-isomer | $NH_2$—$C_6H_5CH_2$ | H | OH | OH |
| I-p | β-D-isomer | Cl—$C_6H_5CH_2$ | H | OH | OH |
| I-q | β-D-isomer | Alkyl—$C_6H_5CH_2$ | H | OH | OH |
| I-r | β-D-isomer | Methoxy—$C_6H_5CH_2$ | H | OH | OH |
| I-s | β-D-isomer | Thiol—$C_6H_5CH_2$ | H | OH | OH |
| I-t | β-D-isomer | F—$C_6H_5CH_2$ | H | $C_6H_5C(O)O$ | OH |
| I-u | β-D-isomer | $NO_2$—$C_6H_5CH_2$ | H | $C_6H_5C(O)O$ | OH |
| I-v | β-D-isomer | $NH_2$—$C_6H_5CH_2$ | H | $C_6H_5C(O)O$ | OH |
| I-w | β-D-isomer | Cl-$C_6H_5CH_2$ | H | $C_6H_5C(O)O$ | OH |
| I-x | β-D-isomer | Alkyl—$C_6H_5CH_2$ | H | $C_6H_5C(O)O$ | OH |
| I-y | β-D-isomer | Methoxy—$C_6H_5CH_2$ | H | $C_6H_5C(O)O$ | OH |
| I-z | β-D-isomer | Thiol—$C_6H_5CH_2$ | H | $C_6H_5C(O)O$ | OH |
| I-a' | β-D-isomer | H | OH | H | OH |
| I-b' | β-D-isomer | $CH_3$ | OH | H | OH |
| I-c' | β-D-isomer | $CH_3CH_2$ | OH | H | OH |
| I-d' | β-D-isomer | $CH_3CH_2CH$ | OH | H | OH |
| I-e' | β-D-isomer | BrCH=CH | OH | H | OH |
| I-f' | β-D-isomer | $C_6H_5CH_2$ | OH | H | OH |
| I-g' | β-D-isomer | H | $C_6H_5C(O)O$ | H | OH |
| I-h' | β-D-isomer | $CH_3$ | $C_6H_5C(O)O$ | H | OH |
| I-i' | β-D-isomer | $CH_3CH_2$ | $C_6H_5C(O)O$ | H | OH |
| I-j' | β-D-isomer | $CH_3CH_2CH$ | $C_6H_5C(O)O$ | H | OH |
| I-k' | β-D-isomer | BrCH=CH | $C_6H_5C(O)O$ | H | OH |
| I-l' | β-D-isomer | $C_6H_5CH_2$ | $C_6H_5C(O)O$ | H | OH |
| I-m' | β-D-isomer | F—$C_6H_5CH_2$ | OH | H | OH |
| I-n' | β-D-isomer | $NO_2$—$C_6H_5CH_2$ | OH | H | OH |
| I-o' | β-D-isomer | $NH_2$—$C_6H_5CH_2$ | OH | H | OH |
| I-p' | β-D-isomer | Cl—$C_6H_5CH_2$ | OH | H | OH |
| I-q' | β-D-isomer | Alkyl—$C_6H_5CH_2$ | OH | H | OH |
| I-r' | β-D-isomer | Methoxy—$C_6H_5CH_2$ | OH | H | OH |
| I-s' | β-D-isomer | Thiol—$C_6H_5CH_2$ | OH | H | OH |
| I-t' | β-D-isomer | F—$C_6H_5CH_2$ | $C_6H_5C(O)O$ | H | OH |
| I-u' | β-D-isomer | $NO_2$—$C_6H_5CH_2$ | $C_6H_5C(O)O$ | H | OH |
| I-v' | β-D-isomer | $NH_2$—$C_6H_5CH_2$ | $C_6H_5C(O)O$ | H | OH |
| I-w' | β-D-isomer | Cl—$C_6H_5CH_2$ | $C_6H_5C(O)O$ | H | OH |
| I-x' | β-D-isomer | Alkyl—$C_6H_5CH_2$ | $C_6H_5C(O)O$ | H | OH |
| I-y' | β-D-isomer | Methoxy—$C_6H_5CH_2$ | $C_6H_5C(O)O$ | H | OH |
| I-z' | β-D-isomer | Thiol—$C_6H_5CH_2$ | $C_6H_5C(O)O$ | H | OH |

As mentioned above, the compounds in Table I are illustrative but not limiting. For example, $R^4$ can be not only hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O and other combinations of the structural elements such as described herein, as well as other stereochemical orientations, are also possible.

In certain embodiments, acyl derivatives of the 2,2'-anhydropyrimidines of formula (I) are of interest. Thus, compounds of formula (I) include those in which $R^1$, $R^2$, $R^3$ and $R^4$ are as defined above, wherein at least one of $R^2$, $R^3$ and $R^4$ is an acyl derivative. By "acyl derivative" is intended a derivative of a 2,2'-anhydropyrimidine of formula (I) in which at least one of $R^2$, $R^3$ and $R^4$ is a substantially nontoxic organic acyl substituent obtainable from a carboxylic acid that is attached to a hydroxyl group on the ribose or pyrimidine ring of formula (I) through an ester linkage.

Acyl derivatives of a 2,2'-anhydropyrimidine compound of formula (I) include those in which $R^1$ is as defined above, and each $R^2$, $R^3$ and $R^4$ is independently hydrogen, hydroxyl or an acyl radical, with the proviso that at least one of $R^2$, $R^3$ and $R^4$ is not hydrogen. In another embodiment, the acyl derivative of a 2,2'-anhydropyrimidine is a compound of formula (I) in which $R^1$ and $R^2$ are as defined above, with the proviso that $R^2$ is other than hydrogen, and each $R^3$ and $R^4$ is independently hydroxyl or an acyl radical. In one embodiment, the acyl derivative of a 2,2'-anhydropyrimidine is a compound of formula (I) in which $R^1$ is as defined above, $R^2$ is hydrogen, and each $R^3$ and $R^4$ is independently hydroxyl or an acyl radical. Of particular interest, is an acyl derivative of a 2,2'-anhydropyrimidine compound of formula (I), wherein $R^1$ is methyl, $R^2$ is hydrogen, and each $R^3$ and $R^4$ is independently hydroxyl or an acyl radical. Also of interest is an acyl derivative of a 2,2'-anhydropyrimidine compound of formula (I), wherein $R^1$ is methyl, $R^2$ is hydrogen, and each $R^3$ and $R^4$ is an acyl radical.

In general, the ester linkage(s) of an acyl derivative of formula (I) are cleavable under physiological conditions, either in vitro, such as in a cell-based system, and/or in vivo, such as through metabolism in a body. Thus, in certain embodiments, the acyl radical is a radical of a metabolite. Such acyl substituents include, but are not limited to, those derived from acetic acid, fatty acids, amino acids, lipoic acid, glycolic acid, lactic acid, enolpyruvic acid, pyruvic acid, orotic acid, acetoacetic acid, beta-hydroxybutyric acid, creatinic acid, succinic acid, fumaric acid, adipic acid, benzoic acid and p-aminobenzoic acid. Particular acyl substituents of interest are compounds which are normally present in the body, either as dietary constituents or as intermediary metabolites, and which are essentially nontoxic when cleaved from the 2,2'-anhydropyrimidine compounds of interest in vivo.

Of particular interest are compositions comprising a 3'-O-acyl-2,2'-anhydropyrimidine or derivative thereof. For example, acyl derivatives of interest are those that include a 2,2'-anhydropyrimidine compound of formula (I), where each $R^1$, $R^2$ and $R^3$ is independently selected from selected from hydrogen, hydroxyl, sulfhydryl, amino, hydroxymethyl, methoxy, halogen, pseudohalogen, and a substituted or unsubstituted lower hydrocarbon containing 1 to 20 carbons, such as a lower hydrocarbon selected from alkyl, alkenyl, alkanoyl, aryl, aroyl, aralkyl and alkylamino, and esters thereof, and where $R^4$ is an O-acyl radical.

In certain embodiments, the acyl derivatives include a 2,2'-anhydropyrimidine compound of formula (I), where $R^4$ is an O-acyl radical, and where the O-acyl radical comprises 1 to 10 carbon atoms, such as an O-acyl radical selected from aryoloxy, aralkyloxy, heteroaryloxy, and cycloalkyloxy.

Accordingly, acyl derivatives of a 2,2'-anhydropyrimidine compound of formula (I) include 3'-O-acyl-2,2'-anhydropyrimidines, 5'-O-acyl-2,2'-anhydropyrimidines, 3',5'-O-acyl-2,2'-anhydropyrimidines, and derivatives thereof. For example, 3'-O-acyl-2,2'-anhydropyrimidines or derivatives thereof include 3'-O-aroyl-2,2'-anhydropyrimidines, such as a 3'-O-aroyl-2,2'-anhydrouridine or derivative thereof. An example of particular interest is 3'-O-benzoyl-2,2'-anhydrouridine or derivative thereof, such as 3'-O-benzoyl-2,2'-anhydro-5-methyluridine. Also of interest is a compound in which the 3'-O-benzoyl-2,2'-anhydro-5-methyluridine is the stereoisomer 3'-O-benzoyl-2,2'-anhydro-1-(β-D-arabinofuranosyl)-5-methyluracil.

In some embodiments, acyl derivatives of a 2,2'-anhydropyrimidine compound of formula (I) include those where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH═CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH═CH, phenyl, phenyloxy, benzyl, benzyloxy, benzoyl, benzyloxybenzyl, or acyl radical, and where each $R^3$ and $R^4$ is independently hydroxyl or an acyl radical. These include the compounds: 3'-O-benzoyl-2,2'-anhydrouridine; 3'-O-benzoyl-2,2'-anhydro-5-fluorouridine; 3'-O-benzoyl-2,2'-anhydro-5-trifluoromethyluridine; 3'-O-benzoyl-2,2'-anhydro-5-methyluridine; 3'-O-benzoyl-2,2'-anhydro-5-ethyluridine; 3'-O-benzoyl-2,2'-anhydro-5-propyluridine; 3'-O-benzoyl-2,2'-anhydro-5-isopropyluridine; 3'-O-benzoyl-2,2'-O-anhydro-5-isobutyluridine; 3'-O-benzoyl-2,2'-anhydro-5-methylacyluridine; 3'-O-benzoyl-2,2'-anhydro-5-propylacyluridine; 3'-O-benzoyl-2,2'-anhydro-5-(2-bromovinyl)-uridine; 3'-O-benzoyl-2,2'-anhydro-5-phenylluridine; 3'-O-benzoyl-2,2'-anhydro-5-benzyluridine; 3'-O-benzoyl-2,2'-anhydro-5-benzyoluridine; and 3'-O-benzoyl-2,2'-anhydro-5-(benzyloxybenzyl)-uridine; 5'-O-benzoyl-2,2'-anhydrouridine; 5'-O-benzoyl-2,2'-anhydro-5-fluorouridine; 5'-O-benzoyl-2,2'-anhydro-5-trifluoromethyluridine; 5'-O-benzoyl-2,2'-anhydro-5-methyluridine; 5'-O-benzoyl-2,2'-anhydro-5-ethyluridine; 5'-O-benzoyl-2,2'-anhydro-5-propyluridine; 5'-O-benzoyl-2,2'-anhydro-5-isopropyluridine; 5'-O-benzoyl-2,2'-O-anhydro-5-isobutyluridine; 5'-O-benzoyl-2,2'-anhydro-5-methylacyluridine; 5'-O-benzoyl-2,2'-anhydro-5-propylacyluridine; 5'-O-benzoyl-2,2'-anhydro-5-(2-bromovinyl)-uridine; 5'-O-benzoyl-2,2'-anhydro-5-phenylluridine; 5'-O-benzoyl-2,2'-anhydro-5-benzyluridine; 5'-O-benzoyl-2,2'-anhydro-5-benzyoluridine; and 5'-O-benzoyl-2,2'-anhydro-5-(benzyloxybenzyl)-uridine; 3',5'-O-benzoyl-2,2'-anhydrouridine; 3',5'-O-benzoyl-2,2'-anhydro-5-fluorouridine; 3',5'-O-benzoyl-2,2'-anhydro-5-trifluoromethyluridine; 3',5'-O-benzoyl-2,2'-anhydro-5-methyluridine; 3',5'-O-benzoyl-2,2'-anhydro-5-ethyluridine; 3',5'-O-benzoyl-2,2'-anhydro-5-propyluridine; 3',5'-O-benzoyl-2,2'-anhydro-5-isopropyluridine; 3',5'-O-benzoyl-2,2'-O-anhydro-5-isobutyluridine; 3',5'-O-benzoyl-2,2'-anhydro-5-methylacyluridine; 3',5'-O-benzoyl-2,2'-anhydro-5-propylacyluridine; 3',5'-O-benzoyl-2,2'-anhydro-5-(2-bromovinyl)-uridine; 3',5'-O-benzoyl-2,2'-anhydro-5-phenylluridine; 3',5'-O-benzoyl-2,2'-anhydro-5-benzyluridine; 3',5'-O-benzoyl-2,2'-anhydro-5-benzyoluridine; and 3',5'-O-benzoyl-2,2'-anhydro-5-(benzyloxybenzyl)-uridine; or the pharmaceutically acceptable salts, solvates, hydrates, and prodrug forms thereof, and stereoisomers thereof.

Of specific interest is 3'-O-benzoyl-2,2'-anhydro-5-methyluridine, 5'-O-benzoyl-2,2'-anhydro-5-methyluridine, and 3',5'-O-benzoyl-2,2'-anhydro-5-methyluridine, or the pharmaceutically acceptable salts, solvates, hydrates, and prodrug forms thereof, and stereoisomers thereof. Of specific interest are the β-D-arabinofuranosyl isomers of these compounds, or the pharmaceutically acceptable salts, solvates, hydrates, and prodrug forms thereof.

In another embodiment, compounds according to formula (I) of specific interest are those where $R^1$ and $R^4$ are as defined above, and $R^2$ and/or $R^3$ is a cyclic hydrocarbyl. By "cyclic hydrocarbyl" is intended a hydrocarbon-based ring structure having from 3 to about 10 carbon atoms and having a single cyclic ring or multiple condensed rings that may be substituted. Cyclic hydrocarbyls of interest are selected from aryl, aralkyl, aryloxy, aroyl, aryoxyloxy, heteroaryl, heteroaryloxy, heteroaryoloxy, cycloalkyl, cycloalkyloxy and cycloalkyloxy. Thus, cyclic hydrocarbyls of special interest are O-linked to the ribose or pyrimidine ring of formula (I). Compounds where $R^2$ and/or $R^3$ is a cyclic hydrocarbyl exhibit improved activity on a molar basis, or improved specificity with respect to not interfering with cancer therapy efficacy.

Accordingly, certain compounds of the invention comprise a 5'-O-(cyclic hydrocarbyl)-2,2'-anhydropyrimidine or derivative thereof. This embodiment includes 5'-O-(cyclic hydrocarbyl)-2,2'-anhydro-5($R^5$)-uridine or derivatives thereof, where $R^5$ is $R^1$ (e.g., $R^5$=$R^1$ where "5($R^5$)" refers to and is the same as $R^1$ of formula (I)).

A compound of interest is 5'-O-aryl-2,2'-anhydropyrimidine or derivative thereof, of which various 2,2'-anhydrouridine derivatives are of included. This includes compounds where the 5'-O-aryl-2,2'-anhydropyrimidine is a 5'-O-aroyl-2,2'-anhydropyrimidine, such as: 5'-O-benzoyl-2,2'-anhydropyrimidine; 5'-O-chlorobenzyl-2,2'-anhydropyrimidine; 5'-O-nitrobenzyl-2,2'-anhydropyrimidine; 5'-O-hydroxybenzyl-2,2'-anhydropyrimidine, and the like.

In one embodiment, compounds that exhibit improved activity on a molar basis or improved specificity with respect to not interfering with fluorouracil therapy efficacy are the 5'-O-aryl-2,2'-anhydrouridines, 5'-O-aroyl-2,2'-anhydrouridines, and derivatives thereof, such as 5'-O-aryl-2,2'-anhydro-5($R^4$)-uridine, 5'-O-aroyl-2,2'-anhydro-5($R^4$)-uridine, and their derivatives. Examples include 5'-O-aryl-2,2'-anhydro-5-methyl-uridine; 5'-O-aryl-2,2'-anhydro-5-ethyl-uridine; 5'-O-aryl-2,2'-anhydro-5-propyl-uridine; 5'-O-aryl-2,2'-anhydro-5-benzyl-uridine; and 5'-O-aryl-2,2'-anhydro-5-(2-bromovinyl)-uridine; and derivatives thereof. Examples also include 5'-O-aroyl-2,2'-anhydro-5-methyl-uridine; 5'-O-aroyl-2,2'-anhydro-5-ethyl-uridine; 5'-O-aroyl-2,2'-anhydro-5-propyl-uridine; 5'-O-aroyl-2,2'-anhydro-5-benzyl-uridine; and 5'-O-aroyl-2,2'-anhydro-5-(2-bromovinyl)-uridine; and derivatives thereof. Compounds of specific interest include 5'-O-benzoyl-2,2'-anhydro-5($R^4$)-uridines, such as 5'-O-benzoyl-2,2'-anhydro-5-methyl-uridine; 5'-O-benzoyl-2,2'-anhydro-5-ethyl-uridine; 5'-O-benzoyl-2,2'-anhydro-5-propyl-uridine; 5'-O-benzoyl-2,2'-anhydro-5-benzyl-uridine; and 5'-O-benzoyl-2,2'-anhydro-5-(2-bromovinyl)-uridine.

Stereoisomers of interest include the 5'-O-(cyclic hydrocarbyl)-2,2'-anhydropyrimidines which are the β-D-isomers. Examples include, but are not limited to: 5'-O-benzoyl-2,2'-anhydro-1-(β-D-arabinofuranosyl)uracil; 5'-O-benzoyl-2,2'-anhydro-1-(β-D-arabinofuranosyl)-5-fluorouracil; 5'-O-benzoyl-2,2'-anhydro-1-(β-D-arabinofuranosyl)-5-trifluoromethyluracil; 5'-O-benzoyl-2,2'-anhydro-1-(β-D-arabinofuranosyl)-5-methyluracil; 5'-O-benzoyl-2,2'-anhydro-1-(β-D-arabinofuranosyl)-5-ethyluracil; 5'-O-benzoyl-2,2'-anhydro-1-(β-D-arabinofuranosyl)-5-n-propyluracil; 5'-O-benzoyl-2,2'-anhydro-1-(β-D-arabinofuranosyl)-5-isopropyluracil; 5'-O-benzoyl-2,2'-anhydro-1-(β-D-arabinofuranosyl)-5-isobutyluracil; 5'-O-benzoyl-2,2'-anhydro-1-(β-D-arabinofuranosyl)-5-methyacyluracil; 5'-O-benzoyl-2,2'-anhydro-1-(β-D-arabinofuranosyl)-5-propylacyluracil; 5'-O-benzoyl-2,2'- anhydro-1-(β-D-arabinofuranosyl)-5-(2-bromovinyl)uracil; 5'-O-benzoyl-2,2'-anhydro-1-(β-D-5'-O-benzoyl-2,2'-anhydro-1-(β-D-arabinofuranosyl)-5-phenyluracil; 5'-O-benzoyl-2,2'-anhydro-1-(β-D-arabinofuranosyl)-5-benzyluracil; arabinofuranosyl)-5-benzyoluracil; and 5'-O-benzoyl-2, 2'-anhydro-1-(β-D-arabinofuranosyl)-5-(3-benzyoxybenzyl)uracil.

As noted above, also of interest are analogues/derivatives of the above compounds, where such analogs/derivatives reduce cancer therapy toxicity, such that cancer therapy toxicity is reduced when the compounds are administered in conjunction with a cancer therapy according to the subject invention. As also indicated above, an effective amount of cancer therapy toxicity-reducing adjuvant is employed in the subject methods.

The 2,2'-anhydropyrimidine and derivatives thereof described above are commercially available or can be conventionally prepared by techniques known to one of skill in the art. For example, representative patents describing various 2,2'-anhydropyrimidine and derivatives, including intermediates and precursors, analysis, as well as the synthesis/preparation thereof, include U.S. Pat. Nos. 3,975,367; 4,145,531; 4,230,698; 4,247,544; 4,544,740; 4,604,382; 4,613,604; 4,681,933; 4,841,039; 4,916,122; 4,987,224; 5,008,384; 5,077,280; 5,084,445; 5,141,943; 5,190,926; 5,212,293; 5,278,167; 5,384,396; 5,455,339; 5,476,855; 5,596,093; 5,610,292; 5,721,241; 5,723,449; 5,739,314; 5,760,202; 5,889,013; 5,861,493; 6,060,592; 6,090,932; 6,222,025; 6,369,040; 6,642,367; 6,670,461; 6,867,290; and 7,176,295; the disclosures of which are herein incorporated by reference. See also, the following references: Veres et al., Biochem Pharmacol. 34(10):1737 (1985); Veres et al., Drugs Exp Clin Res. 13(10):615 (1987); el Konui et al, Mol. Pharmacology 34:104 (1988); Cienfuegos et al. Org. Lett. 7(11):2161 (2005); Choi et al., Nucleosides Nucleotides Nucleic Acids 22(5-8):547 (2003); Rodriquez et al., J Med Chem 37(20):3389 (1994); McGee, D. P. C. et al., "Novel Nucleosides via Intramolecular Functionalization of 2,2' Anahydrouridine Derivatives", Tetr. Lett., 37(12):1995 (1996); Machulla et al. J. Nucl. Med. 42(5):257 (2001); Czernecki S. et al. Nucleosides & Nucleotides 14:1227 (1995); Heterocyclic Chemistry (3rd Edition), Thomas. L. Gilchrist, Prentice Hall (1997); Movassaghi, M. and M. D. Hill, J. Am. Chem. Soc. 128(44):14254 (2006); Brown, D. J. Heterocyclic Compounds: The Pyrimidines. Vol 52. New York: Interscience, 1994; Eaton, (1995) Annu. Rev. Biochem. 64, 837; Usman and Cedergreen TIBS 17:334 (1992); Greene and Wuts (1991) Protective Groups in Organic Synthesis, 2nd Ed., Wiley Interscience); Moffatt, (1979) Nucleoside Analogues, Ed. Walker, NY, Plenum.; Townsend, (1988) Chemistry of Nucleosides and Nucleotides, NY, Plenum; and Sproat, et al., (1991) Oligonucleotides and Analogues: A Practical Approach, ed. F. Eckstein, NY. Oxford Univ. Press)).

Of particular interest are 2,2'-anhydropyrimidines and derivatives thereof that are inhibitors of uridine phosphorylase. Uridine phosphorylase (UPh; EC 2.4.2.3) is a member of the pyrimidine nucleoside phosphorylase family of enzymes which catalyzes the phosphorolytic cleavage of the C—N glycoside bond of uridine, with the formation of ribose 1-phosphate and uracil (Timofeev et al., Acta Crystallogr Sect F Struct Biol Cryst Commun., 63: 852-854 (2007)).

The scope of the present invention includes prodrugs of the cancer therapy toxicity-reducing adjuvant. Such prodrugs are, in general, functional derivatives of the compounds that are readily convertible in vivo into the required compounds. Thus, in the methods of the present invention, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein suitable for the present invention. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

As summarized above, in methods of the invention the cancer therapy toxicity-reducing adjuvant is administered in conjunction with a uridine plasma level modulator. A uridine plasma level modulator is an agent that changes the plasma uridine level of a subject following administration to the subject. In some instances, the uridine plasma level modulator enhances the plasma uridine level in the subject. While the magnitude of any enhancement may vary, in some instances the magnitude of enhancement is 2-fold or greater, such as 5-fold or greater, 10-fold or greater, 15-fold or greater, 20-fold or greater, 25-fold or greater, or 50-fold or greater. A variety of different types of plasma uridine level enhancing agents may be employed. Plasma uridine level enhancing agents include, but are not limited to, uridine and sources thereof, uridine precursors as sources thereof, and uridine degradation inhibitors, such as Uridine phosphorylase (UPase) inhibitors, uridine secretion inhibiting compounds and uridine renal transport competitors.

Uridine and sources thereof include, but are not limited to meat products, such as fish, pig and cow liver and pancreas, and the like; fungi related products, such as brewer's yeast, beer, mushrooms, and the like; vegetable products, such as sugarcane, tomatoes, oats, algae, broccoli and the like; salts, such as uridine phosphates, acylated uridine, and the like. Uridine and sources thereof which may be employed in embodiments of the invention include, but are not limited to, those described in U.S. Pat. Nos.: 9,579,337; 6,316,426; and 5,470,838; the disclosures of which compounds are incorporated herein by reference.

Uridine precursors and sources thereof include, but are not limited to: prodrugs of uridine, such as triphenyluridine, orotic acid and the like; prodrugs of uridine 5'-monophosphate, such as mono- and di-alkyl esters, acyloxyalkyl esters, alkoxycarbonylmethyl esters, substituted ethyl and propyl esters, amidomethyl esters, benzyl esters phenyl esters, phosphonamidates, cyclophosphate esters and the like; uridine prodrugs containing mono-, di- or tri-esters of uridine, such as mono-, di-, and triacetyl uridine and the like; uridine prodrugs containing mono, di- or tri-phosphates of uridine, such as uridine monophosphate, uridine diphosphate, uridine triphosphate and the like; uridine homodimers and their esters, such as U-P-U and the like; heterodimers of dideoxynucleoside compounds and uridine or uridine phosphorylase inhibitors, such as AZT-P-U and AZT-P-BAU; etc. Uridine precursors and sources thereof which may be employed in embodiments of the invention include, but are not limited to, those described in U.S. Pat. Nos.: 5,723,449 and 7,737,128; the disclosures of which compounds are incorporated herein by reference.

Uridine phosphorylase (UPase) inhibitors include, but are not limited to: benzylacyclouridine, benzyloxyacylouridine, aminomethyl-benzylacyclouridine, aminomethyl-benzyloxybenzylacyclouridine, hydroxymethyl-benzylacyclouridine, hydroxymethyl-benzyloxybenzyl acyclouridine, and the like; derivatives of 5-benzylbarbiturate, such as 5-benzyloxybenzyl barbiturate; 5-benzyloxybenzyl-1-(1-hydroxy-2-ethoxy)methyl) barbiturate; 5-benzyloxybenzylacetyl-1-(1-hydroxy-2-ethoxy) methyl) barbiturate; 5-benzyloxybenzyl-1-(1,3-dihydroxy 2-propoxy)methyl barbiturate; 5-benzyloxybenzyl-1-1-hydroxy, 3-amino-2-propoxy)methyl) barbiturate; 5-benzyloxybenzyl-1-(2-(3-carboxypropionyloxy)ethoxy) methyl) barbiturate; 5-benzyl-1-(1-hydroxy-2-ethoxy) methyl) barbiturate; 5-methoxybenzylacetyl barbiturate; 5-benzyl-1-(1,3-dihydroxy-2-propoxy)methyl) barbiturate; 5-benzyl-1-(1-hydroxy, 3-amino-2-propoxy)methyl) barbiturate; and 5-benzyl-1-(2-(3-carboxypropionyloxy)ethoxy) methyl) barbiturate, and the like. Upase inhibitors which may be employed in embodiments of the invention include, but are not limited to, those described in U.S. Pat. Nos.: 5,723,449; 5,141,943; 5,077,280; and 4,613,604; the disclosures of which compounds are incorporated herein by reference.

Uridine secretion inhibiting compounds include, but are not limited to drugs, such as dilazep, hexobendine. Uridine secretion inhibiting compounds which may be employed in embodiments of the invention include, but are not limited to, those described in U.S. Pat. Nos.: 6,989,376 and 5,567,689; the disclosures of which compounds are incorporated herein by reference.

Uridine renal transport competitors include, but are not limited to drugs, such as L-uridine, L-2',3'-dideoxyuridine, D-2',3'-dideoxyuridine. Uridine renal transport competitors which may be employed in embodiments of the invention include, but are not limited to, those described in U.S. Pat. Nos.: 6,989,376; 5,723,449 and 5,567,689; the disclosures of which compounds are incorporated herein by reference.

Subjects that are treated according to methods of the invention may be subjects undergoing cancer therapy. Treatment according to the disclosed methods can begin prior to cancer therapy associated with mucositis (e.g., prophylactically, and/or 1-2 days or up to 1 week prior), at or near the same time as cancer therapy associated with mucositis (e.g., simultaneously with, within 1-4 hours of, or on the same day as the treatment), or shortly after the cessation of cancer therapy associated with mucositis (e.g., within 1-4 days of cessation, and/or prior to or upon appearance of symptoms). Treatment can then be maintained, for example, until any symptoms of mucositis have substantially cleared or the risk of developing such symptoms has passed. Thus, treatment started before or at or near the same time as cancer therapy associated with mucositis can be maintained, e.g., for 1-3, e.g., 1-2 days. In other examples, treatment is maintained for 1-4 or 2-3 weeks following the cessation of cancer therapy associated with mucositis, as determined to be appropriate by one of skill in the art. In specific examples, the treatment according to the present disclosure is carried out only prior to cancer therapy associated with mucositis; prior to and concurrently with cancer therapy associated with mucositis; prior to, concurrently with, and after cessation of cancer therapy associated with mucositis; concurrently with cancer therapy associated with mucositis only; concurrently with and after cessation of cancer therapy associated with mucositis only; after cessation of cancer therapy associated with mucositis only; or prior to and after cessation of cancer therapy associated with mucositis only. Further, treatment according to the methods of the present disclosure can be altered, stopped, or re-initiated in a patient, depending on the status of any symptoms of mucositis. Treatment can be carried out at intervals determined to be appropriate by those of skill in the art. For example, the administration can be carried out 1, 2, 3, 4 or more times/day.

The therapy may be radiation and/or administration of one or more chemotherapeutic agents. Chemotherapeutic agents likely to cause oral mucositis include but are not limited to anthracyclines (such as daunorubicin, doxorubicin, pirubicin, idarubicin and mitoxantrone), methotrexate, dactinomycin, bleomycin, vinblastine, cytarabin, fluorouracil, mitramycine, etoposide, floxuridine, 5-fluorouracil, hydroxyurea, methotrexate, mitomycin, vincristine, vinorelbine, taxanes (such as docetaxel and paclitaxel), ifosfamide/eoposide, irinotecan, platinum, as well as combinations including one or more of these drugs. The risk of developing mucositis is markedly exacerbated when chemotherapeutic agents that typically produce mucosal toxicity are given in high doses, in frequent repetitive schedules, or in combination with ionizing irradiation (e.g., conditioning regimens prior to bone marrow transplant). The lesions induced by chemotherapeutic agents are clinically significant by about a week after treatment and the severity progresses to about day ten through twelve and begins to subside by day fourteen. Accordingly, in some embodiments, the patient to be treated is one undergoing or scheduled to undergo treatment with one or more of these chemotherapeutic agents.

Formulations

Also provided are pharmaceutical compositions containing the cancer therapy toxicity-reducing adjuvant and/or uridine plasma level modulator employed in the subject methods. Accordingly, the cancer therapy toxicity-reducing adjuvant and/or plasma uridine level modulator may be present in pharmaceutical compositions, e.g., in the form of a pharmaceutically acceptable salt, and can be formulated for oral, topical, or parenteral administration for use in the subject methods, as described above. In certain embodiments, e.g., where the compounds are administered as separate formulations (such as in those embodiments where they are administered sequentially), separate or distinct pharmaceutical compositions, each containing a different active agent, are provided. In yet other embodiments, a single formulation that includes both the cancer therapy toxicity-reducing adjuvant and the uridine plasma level modulator (i.e., one composition that includes both active agents) is provided.

By way of illustration, the cancer therapy toxicity-reducing adjuvant and/or uridine plasma level modulator can be admixed with conventional pharmaceutically acceptable carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1% to about 90% by weight of the active compound, and more generally from about 1% to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example, a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils, and colloidal silica.

Flavoring agents such as peppermint, oil of wintergreen, cherry flavoring, or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, *arachis* oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetracetic acid, and an antioxidant, for example, sodium metabisulphite may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, herein incorporated by reference in its entirety. Such patches may be constructed for continuous, pulsatile, or on demand delivery of pharmaceutical agents.

In certain embodiments of interest, the cancer therapy toxicity-reducing adjuvant and uridine plasma level modulator are administered as a single pharmaceutical formulation, that, in addition to including an effective amount of the cancer therapy toxicity-reducing adjuvant and uridine plasma level modulator, includes other suitable compounds and carriers, and may also be used in combination with other active agents. The present invention, therefore, also includes pharmaceutical compositions comprising pharmaceutically acceptable excipients. The pharmaceutically acceptable excipients include, for example, any suitable vehicles, adjuvants, carriers or diluents, and are readily available to the public. The pharmaceutical compositions of the present invention may further contain other active agents that are well known in the art.

One skilled in the art will appreciate that a variety of suitable methods of administering a formulation of the present invention to a subject or host, e.g., patient, in need thereof, are available, and, although more than one route can be used to administer a particular formulation, a particular route can provide a more immediate and more effective reaction than another route. Pharmaceutically acceptable excipients are also well-known to those who are skilled in the art and are readily available. The choice of excipient will be determined in part by the particular compound, as well as by the particular method used to administer the composition. Accordingly, there are a wide variety of suitable formulations of the pharmaceutical composition of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The subject formulations of the present invention can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, and other such carriers that are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Those of skill in the art will readily appreciate that dose levels can vary as a function of the specific compound, the nature of the delivery vehicle, and the like. Suitable dosages for a given compound are readily determinable by those of skill in the art by a variety of means.

The dose administered to an animal, particularly a human, in the context of the present invention should be sufficient to cause a prophylactic or therapeutic response in the animal over a reasonable time frame. One skilled in the art will recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Suitable doses and dosage regimens can be determined by comparisons to anticancer or immunosuppressive agents that are known to cause the desired growth inhibitory or immunosuppressive response.

Optionally, the pharmaceutical composition may contain other pharmaceutically acceptable components, such as buffers, surfactants, antioxidants, viscosity modifying agents, preservatives and the like. Each of these components is well-known in the art. For example, see U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985). In an embodiment, the aqueous solution of cyclodextrin also contains dextrose, e.g., about 5% dextrose.

Utility

The subject methods find use in the treatment of cellular proliferative disease conditions, e.g., cancers and related conditions characterized by abnormal cellular proliferation. Such disease conditions include cancer and neoplastic diseases and other diseases characterized by the presence of unwanted cellular proliferation, e.g., hyperplasias, and the like. Autoimmune diseases like multiple sclerosis also feature inappropriate proliferation of immune cells.

By treatment, is meant that at least an amelioration of the symptoms associated with the condition afflicting the host is achieved, where amelioration is used in a broad sense to refer to at least a reduction in the magnitude of a parameter, e.g., a symptom associated with the condition being treated or a side effect resulting from administration of a drug. As such, treatment also includes situations where the pathological condition, or at least symptoms associated therewith, are completely inhibited, e.g., prevented from happening, or stopped, e.g., terminated, such that the host no longer suffers from the condition, or at least the symptoms that characterize the condition.

A specific application of interest is the use of the subject methods to treat cancer therapy-induced mucositis, e.g., stomatitis. In some instances, the target mucositis is characterized by one or more features selected from myelosuppression, weight loss, inflammation, and infection. Reduction of cancer therapy-induced mucositis is characterized by the prevention, mitigation, or reduction of the likelihood of onset of mucositis resulting from treatment of a host with a given cancer therapy. This includes treatment of a host in need thereof with a cancer therapy in conjunction with an amount of an cancer therapy toxicity-reducing adjuvant and a plasma uridine level modulator effective to reduce cancer therapy-induced mucositis in the host, where the method improves the likelihood of successfully preventing or eliminating one or more features of mucositis when it has occurred including: (i) prevention, that is, causing the clinical symptoms not to develop, e.g., preventing myelosuppression, weight loss, inflammation, and/or infection, and/or preventing progression of one or more of these features to a harmful state; (ii) inhibition, that is, arresting the development or further development of clinical symptoms, e.g., mitigating or completely inhibiting an active (ongoing) feature of mucositis so that the feature is decreased to the degree that it is no longer seriously harmful, which decrease can include complete elimination of mucositis from the host; and/or (iii) relief, that is, causing the regression of clinical symptoms, e.g., causing a relief of myelosuppression, weight loss, inflammation, infection, and/or other symptoms caused by treatment of the host with an fluorouracil active agent.

For example, mucositis severity, including oral mucositis (stomatitis), can easily be assessed by visual inspection of mouth, throat and/or anal lesions associated with the condition, interrogation of test subjects or patients (do you have soreness of the mouth or throat?) or by use of any, or all, three well accepted disease scales: the five-grade World Health Organization (WHO) oral-toxicity scale (Miller A B et al., Cancer 1981; 47:207-214), the five-grade Radiation Therapy Oncology Group (RTOG) acute radiation-morbidity scoring criteria for mucous membranes, National Cancer Institute common toxicity criteria, version 2.0. Apr. 30, 1999 and the four-grade Western Consortium for Cancer Nursing Research (WCCNR) revised staging system for oral mucositis. Assessing stomatitis: refinement of the Western Consortium for Cancer Nursing Research (WCCNR) stomatitis staging system (Can Oncol Nurs J 1998; 8:160-165). Thus, the effect of treatment with a fluorouracil toxicity-reducing adjuvant can readily be determined using any, or all, of these test systems. In some instances, weight loss is diminished as compared to a suitable control where the toxicity reducing agent is not employed, such that is 80% or less, e.g., 70% or less, 60% or less, 50% or less, 40% or less, 30% or less, 25% or less, 20% or less, 15% or less, 10% or less including 5% or less of the weight loss observed in a suitable control is observed with use the toxicity-reducing agent. In some instances, no measurable weight loss occurs with the toxicity-reducing agent is employed.

A variety of subjects are treatable according to the subject methods. Generally, such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects will be humans.

In certain embodiments, the subjects will be subjects that have been diagnosed for and are, therefore, in need of administration of the active agent. In certain embodiments, the methods may include diagnosing the subject for the presence of the disease condition to be treated by administration of the active agent.

The subject methods find use in, among other applications, the treatment of cellular proliferative disease conditions, including neoplastic disease conditions, e.g., cancers, and autoimmune diseases. In such applications, an effective amount of the fluorouracil active agent and fluorouracil toxicity-reducing adjuvant is administered to the subject in need thereof. Treatment is used broadly as defined above, to include at least amelioration in one or more of the symptoms of the disease, as well as a complete cessation thereof, as well as a reversal and/or complete removal of the disease condition, i.e., a cure.

There are many disorders associated with a dysregulation of cellular proliferation, e.g., cellular proliferative disorders. The conditions of interest include, but are not limited to, conditions described below.

The subject methods may be employed in the treatment of a variety of conditions where there is proliferation and/or migration of smooth muscle cells, and/or inflammatory cells into the intimal layer of a vessel, resulting in restricted blood flow through that vessel, e.g., neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue re-modeling or repair of reproductive tissue, e.g., uterine, testicular and ovarian carcinomas, endometriosis, squamous and glandular epithelial carcinomas of the cervix, etc. are reduced in cell number by administration of the subject compounds.

Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g. neuroblastoma, gliomas, etc.; hematological malignancies, e.g. childhood acute leukemia, acute myelogenous leukemias, acute lymphocytic leukemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, gestational choriocarcinoma, choriodenoma destruens, hydatidiform mole, epidermoid cancers of the head and neck, trophoblastic neoplasms such as choriocarcinoma, choriodenoma destruens, hydatidiform mole, etc., and the like.

Some cancers of particular interest include breast cancers, which are primarily adenocarcinoma subtypes. Ductal carcinoma in situ (DCIS) is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the higher the chance of lymph node metastases and the worse the prognosis is associated with greater thickness and depth of the local invasion of the melanoma. Melanoma can spread by local extension (through lymphatics) and/or by hematogenous routes to distant sites. Any organ may be involved by metastases, but lungs and liver are common sites.

Other proliferative diseases of interest relate to epidermal hyperproliferation, tissue remodeling and repair. For example, the chronic skin inflammation of psoriasis is associated with hyperplastic epidermal keratinocytes as well as infiltrating mononuclear cells, including CD4+ memory T cells, neutrophils and macrophages.

The methods of the present invention can provide a method of treating many, if not most, malignancies, including tumors derived from cells selected from skin, connective tissue, adipose, breast, lung, stomach, pancreas, ovary, cervix, uterus, kidney, bladder, colon, prostate, central nervous system (CNS), retina and blood, and the like. Representative cancers of interest include, but are not limited to, head, neck and lung tissue (e.g., head and neck squamous cell carcinoma, non-small cell lung carcinoma, small cell lung carcinoma) gastrointestinal tract and pancreas (e.g., gastric carcinoma, colorectal adenoma, colorectal carcinoma, pancreatic carcinoma); hepatic tissue (e.g., hepatocellular carcinoma), kidney and urinary tract (e.g., dysplastic urothelium, bladder carcinoma, renal carcinoma, Wilms tumor), breast (e.g., breast carcinoma); neural tissue (e.g., retinoblastoma, oligodendroglioma, neuroblastoma, and malignant meningioma; skin (e.g., normal epidermis, squamous cell carcinoma, basal cell carcinoma, melanoma, etc.).

The methods of the present invention also can provide a method of treating hematological tissues (e.g., lymphoma, chronic myeloid leukemia (CML), acute promyelocytic leukemia (APL), acute lymphoblastic leukemia (ALL), acute myeloid leukemia (AML), etc., and the like.

The dose administered to an animal, particularly a human, in the context of the present invention should be sufficient to affect a prophylactic or therapeutic response in the animal over a reasonable time frame. One skilled in the art will recognize that dosage will depend on a variety of factors including the strength of the particular compound employed, the dose of cancer therapy, the dosing regimen used for cancer therapy, the condition of the animal, and the body weight of the animal, as well as the severity of the illness and the stage of the disease.

The size of the dose will also be determined by the existence, nature, and extent of any adverse side-effects that might accompany the administration of a particular compound.

In the treatment of some individuals with the compounds of the present invention, it may be desirable to use a high dose regimen in conjunction with a rescue agent for non-malignant cells. In such treatment, any agent capable of rescue of non-malignant cells can also be employed, such as citrovorum factor, folate derivatives, or Leucovorin in addition to the adjuvant. Such rescue agents are well known to those of ordinary skill in the art.

Kits & Systems

Also provided are kits and systems that find use in practicing the subject methods, e.g., as described above. For example, kits and systems for practicing the subject methods may include one or more pharmaceutical formulations, which include one or both of a cancer therapy toxicity-reducing adjuvant and a uridine plasma level modulator. As such, in certain embodiments the kits may include a single pharmaceutical composition, present as one or more-unit dosages, where the composition includes both a cancer therapy toxicity-reducing adjuvant and a plasma uridine level modulator. In yet other embodiments, the kits may include two or more separate pharmaceutical compositions, each containing either a cancer therapy toxicity-reducing adjuvant or a plasma uridine level modulator.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits. For example, a kit according to one embodiment includes as a first component (a) instructions for using a fluorouracil toxicity-reducing adjuvant, and as a second component (b) a pharmaceutical composition comprising a fluorouracil toxicity-reducing adjuvant, a fluorouracil active agent, or a combination thereof.

Kits of specific interest are those that include a 2, 2'-anhydropyrimidine pharmaceutical composition of the invention and suitable for practicing the subject methods of the invention, such as for reducing cancer therapy-induced mucositis, including stomatitis, and such as for treatment of a cellular proliferative disorder.

The term "system" as employed herein refers to a collection of a cancer therapy toxicity-reducing adjuvant and a plasma uridine level modulator, present in a single or disparate composition, that are brought together for the purpose of practicing the subject methods. For example, separately obtained fluorouracil active agent and fluorouracil toxicity-reducing adjuvant dosage forms brought together and co-administered to a subject, according to the present invention, are a system according to the present invention.

The following examples further illustrate the present invention but should not be construed in any way as limiting its scope.

Experimental

Figure 2:
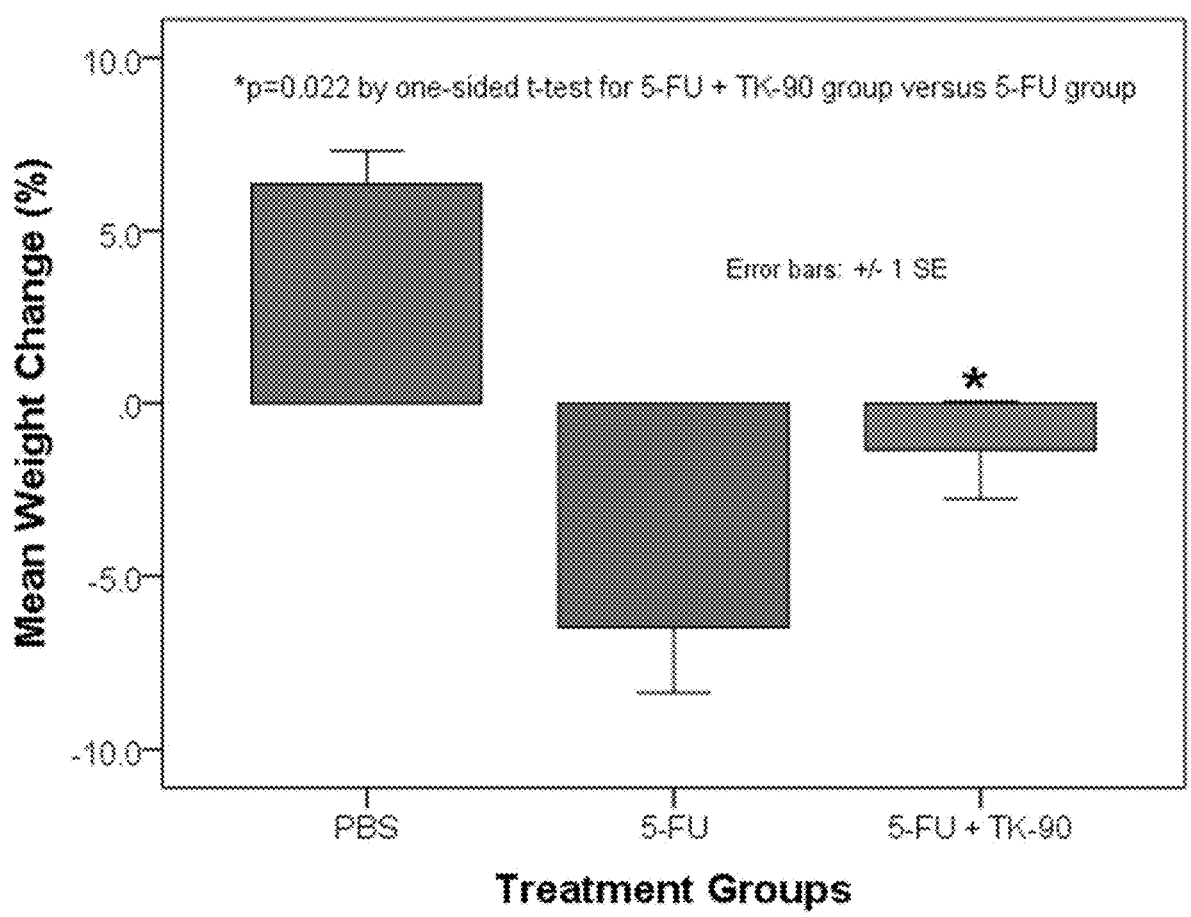
FIG. 2 depicts percent weight change on Day 5 versus Day 0 for CD1 male mice dosed on Day 0 with PBS, 400 mg/kg 5-FU ip, or 400 mg/kg 5-FU ip and 5333 mg/kg sc TK-90 infused using osmotic pumps over 24 hours. Mouse group numbers were n=4, 7, 8 female CD-1 mice for PBS, 5-FU and 5-FU+TK-90 groups, respectively. In this study, TK-90 protected from the weight loss induced by the 5-FU.

I. Protection by a 2,2'-Anhydropyrimidine Test Article for Protection from Weight Loss, One of the Cardinal Features of Mucositis, Induced by a Widely Used Chemotherapeutic The chemotherapeutic challenge was weight loss induced by 5-FU (FIG. 2). As previously mentioned, 5-FU is a widely prescribed anti-cancer drug with substantial mucositis associated with its use. (Miura et al., "5-fu metabolism in cancer and orally administrable 5-fu drugs," Cancers (Basel). (2010) 2(3):1717-30). The aim of this study was to explore whether 5-FU combined with a uridine phosphorylase inhibitor provides protection from weight loss, a principal toxicity of 5-FU.

Groups of CD-1 female mice entrained to light:dark (12:12 hours), and given food and water ad libitum, were used for this experiment. The mean weight of the mice at the start of the experiment was approximately 20 g. Control mice were injected ip with sterile PBS, the vehicle control (Group 1). Group 2 and Group 3 mice were injected, ip, with 400 mg/kg 5-FU (Sigma) dissolved in PBS. A 24-hour osmotic pump (ALZET® micro-osmotic pump, Alza Co) was implanted into Group 3 animals. The pumps were loaded with 200 μL (2001D osmotic pump) of a 500 mg/mL solution of TK-90 (FIG. 2) in PBS. The TK-90 dose over the 24-hour infusion was 5333 mg/kg. The four animals were used for Group 1 and 8 animals were used for Groups 2 and 3. Data for one animal in Group 2 was discarded as an outlier (minimal, inappropriate response to 5-FU).

For the implantation of the osmotic pump, animals were anesthetized with 100 mg/kg ketamine prior to pump implantation. Surgical scissors were used to make an approximately 1 cm incision on the dorsal surface near the shoulder blade of animals. A hemostat was used to carve out a subcutaneous tunnel toward the anterior end of animal. Osmotic pumps were placed inside the subcutaneous tunnel. Incision was sealed with wound clips.

Animals were sacrificed on Day 5 by cervical dislocation and properly disposed. Animal weights were recorded daily for 6 days and the percent difference between Day 0 and Day 5 at termination was calculated.

Results from the study are provided as percent weight gain/loss from pre-dose weight on Day 0 in FIG. 2. Compared to the PBS vehicle control (blue), the 5-FU treatment (red) provided the expected weight loss. By Day 5, the combined uridine and TK-90 treatment (green) provided statistically significant protection compared to the 5-FU group alone ($p<0.04$ comparing Groups 2 and 3).

II. Protection by the 2,2'-Anhydropyrimidine Test Articles Plus Uridine Provided Better Protection Form 5-FU Induced Weight Loss than Uridine Alone.

Weight loss is one of the cardinal features of mucositis. The aim of this study was to explore whether 5-FU combined with a uridine phosphorylase inhibitor and uridine provided better protection from a principal toxicity produced by 5-FU, weight loss, compared to uridine (FIG. 3) alone.

Four groups of male CD-1 mice were treated with daily ip injections of either PBS vehicle (Group 1), 80 mg/kg, 5-FU qdx5 (Groups 2), or 80 mg/kg, 5-FU qdx5 combined with 750 mg/kg uridine, bid, or 80 mg/kg, 5-FU qdx5 combined with 750 mg/kg uridine and 120 mg/kg bid TK-90, a representative 2,2'-anhydropyrimidine test article, sandwiched before and after the uridine doses. Controls include PBS alone at times mimicking the time for 5-FU and combined uridine and TK-90 treatments. There were n=6 animals in all groups.

Animals were sacrificed on Day 5 by cervical dislocation and properly disposed. Animal weights were recorded daily for 6 days and the percent difference between Day 0 and Day 5 at termination calculated.

Figure 3:
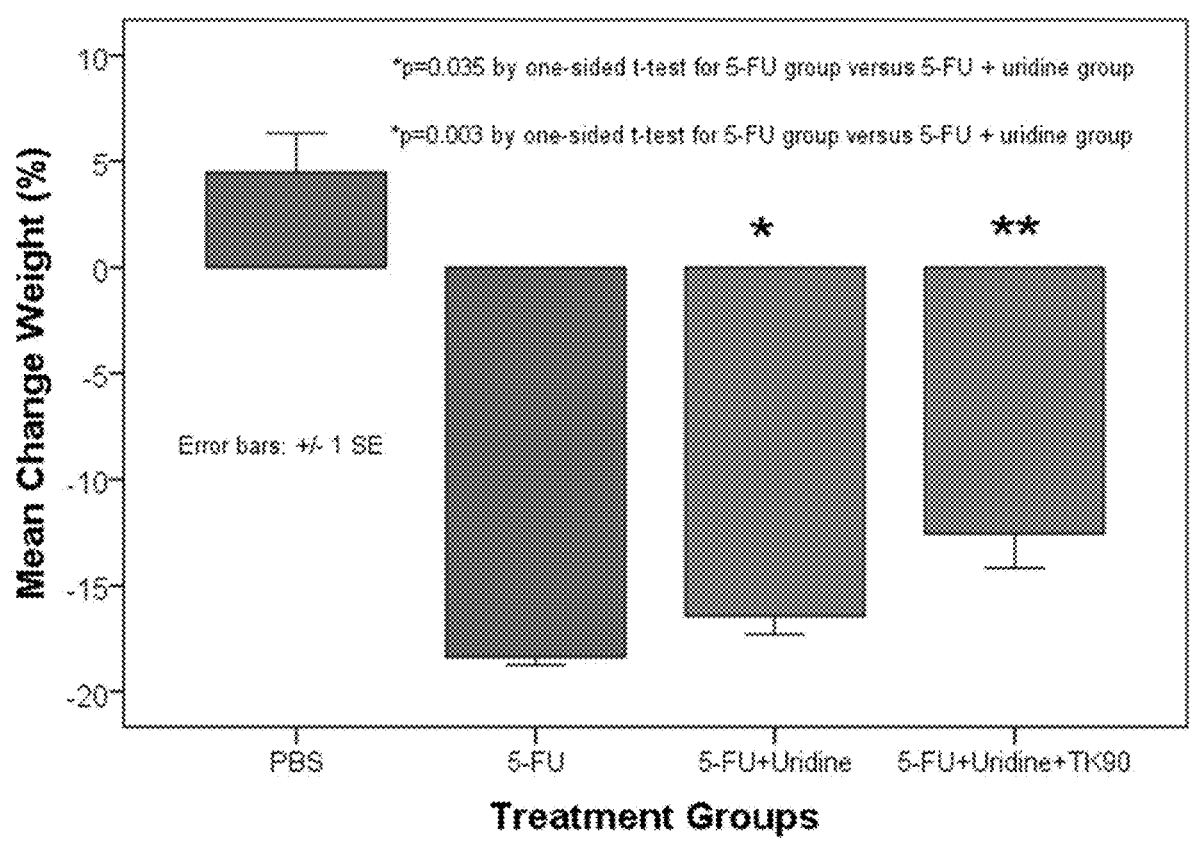
FIG. 3 depicts percent change in CD-1 female mouse weight for Day 5 versus Day 0. Animals were dosed with either PBS ip for 5 days; 750 mg/kg 5-FU, bid, ip for 5 days; or 750 mg/kg 5-FU bid, ip and 120 mg/kg TK-90, bid, for 5 days. Six mice were used for all treatment groups. In this study, TK-90 protected from the weight loss induced by the 5-FU.

Results from the study are provided as percent weight gain/loss from pre-dose weight on Day 0 in FIG. 3. Compared to the PBS vehicle control (blue), the 5-FU treatment (red) provided robust weight loss. By Day 5, the combined uridine and TK-90 treatment (green) provided robust, statistically significant protection compared to the 5-FU group alone ($p<0.003$ for Groups 2 and 4. The statistical difference between Groups 2 and 3 was much less robust ($p=0.036$).

The combined treatments of uridine and a representative 2,2'-anhydropyrimidine test article provided robust, statistically significant protection compared to the 5-FU alone group. The protection provided by uridine was statistically significant but much less than the group with the representative 2,2'-anhydropyrimidine test article.

Results from this experiment indicate that TK-90 is useful to mitigate mucositis associated with 5-FU, including when used in combination with supplemental uridine or a supplement which, when administered, will provide uridine. For certain situations, the supplemental uridine or a uridine producing supplement is beneficial because a high uridine concentration is useful to reverse, or protect from, the induced toxicity. Such situations include where there may be insufficient endogenous uridine present for TK-90 to protect uridine from clearance and thereby elevate the protectant to an effective concentration. In this regard, the clearance of administered uridine is very rapid, having a 3 minute or so half-life in man and animals. (Deng et al., "An adipo-biliary-uridine axis that regulates energy homeostasis," Science (2017) 355(6330): eaaf5375). As a result, the pharmacologic activity of uridine itself without a clearance modulator can only have marginal effects when administered at high doses, even doses that are high enough to cause significant toxicity. With respect to uridine-induced toxicity, clinical studies of high-dose oral uridine have been unsuccessful due to severe patient diarrhea, phlebitis and pyrogenic reactions. Continuous infusions of high-dose uridine have also been unsuccessful because of toxicities, including high fever, cellulitis, and superior vena cava syndrome associated with uridine administration. (van Groeningen et al., "Clinical and pharmacologic study of orally administered uridine," J Natl Cancer Inst. (1991) 83:437-41; van Groeningen et al., "Modulation of fluorouracil toxicity with uridine," Semin Oncol. (1992) 9 (2 Suppl 3):48-54).

III. Protection by a 2,2'-Anhydropyrimidine Test Article from a Decrease in Plasma Citrulline, a Well-Accepted Surrogate Marker for Mucositis.

The chemotherapeutic challenge was diminished plasma citrulline by 5-FU treatment. The aim of this study was to explore whether a uridine phosphorylase inhibitor could prevent lowered plasma citrulline induced by 5-FU.

Groups of C57BL/6 female mice entrained to light:dark (12:12 hours), and given food and water ad libitum, were used for this experiment. The mean weight of the mice at the start of the experiment was approximately 20 g. Control mice were injected ip with sterile PBS, the vehicle control (Group 1). Group 2 and Group 3 mice were injected, ip, with 200 mg/kg 5-FU (Sigma) dissolved in DMSO. Four hours after the 5-FU injection, a 24-hour osmotic pump (ALZET® micro-osmotic pump, Alza Co) was implanted into Group 3 animals. The pumps were loaded with 200 μL (2001D osmotic pump) of a 500 mg/mL solution of TK-90 in PBS. TK-90 solution was prepared at a concentration of 500 mg/mL in sterile PBS. Eight animals were used for Groups 1,2 and 3.

For the implantation of the osmotic pump, animals were anesthetized with 100 mg/kg ketamine prior to pump implantation. Surgical scissors were used to make an approximately 1 cm incision on the dorsal surface near the shoulder blade of animals. A hemostat was used to carve out a subcutaneous tunnel toward the anterior end of animal. Osmotic pumps were placed inside the subcutaneous tunnel. Incision was sealed with Vetbond tissue adhesive and wound clips.

Blood collections were done to animals anesthetized with ketamine (ip 100 mg/kg). Whole blood (~0.8 mL) was drawn through the retro-orbital sinus using a heparin coated micro-hematocrit tube and collected into a heparin microtainer tube. Blood samples were transferred into fresh 1.5 mL microcentrifuge tubes and centrifuged for 5 minutes at 10,000×g using an Eppendorf Minispin Plus stored in a 4° C. refrigerator. Following collection of the plasma samples, the animals were sacrificed on Day 3 by cervical dislocation and properly disposed. The plasma samples were kept frozen until thawed for analysis.

Figure 4:
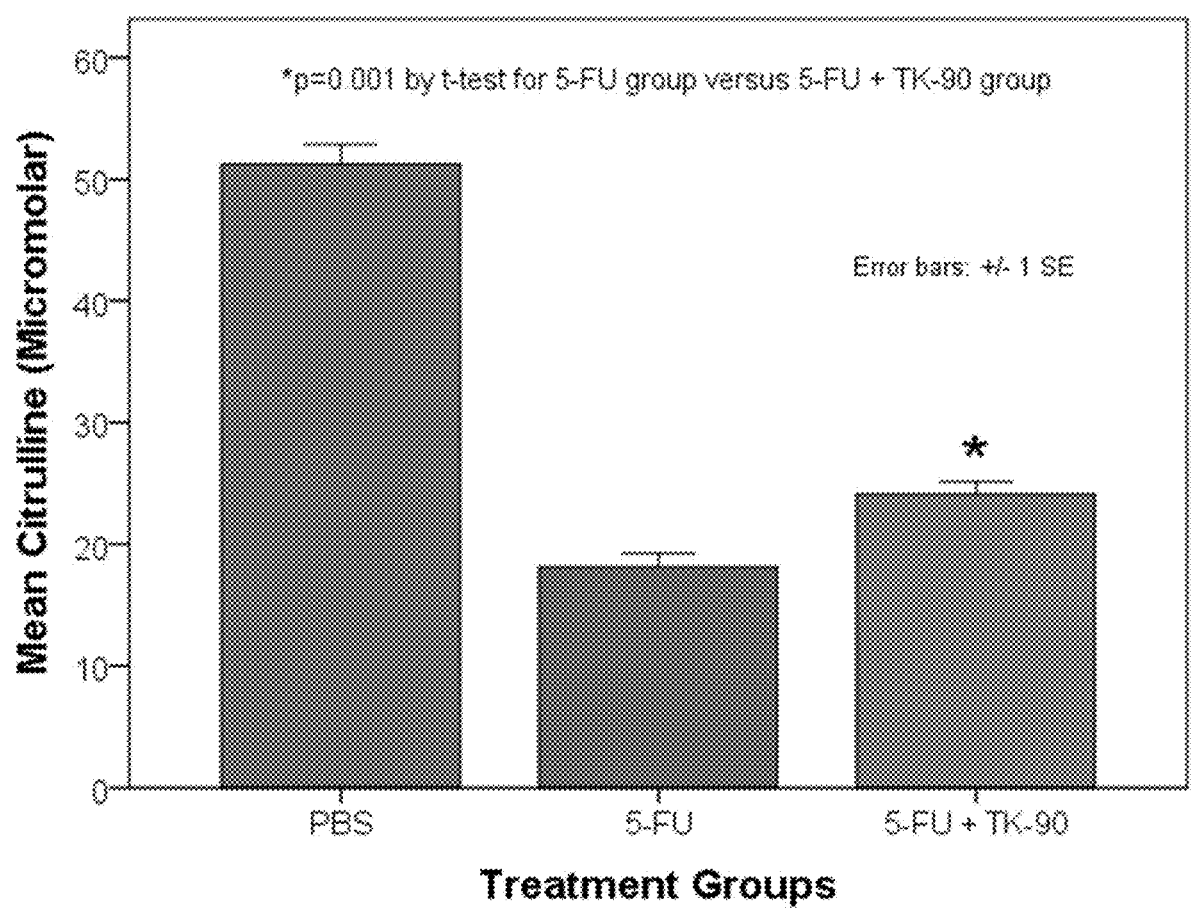
FIG. 4 depicts citrulline concentrations measured in plasma obtained at sacrifice on Day 3 from C57BL/6 female mice treated on Day 0 with either PBS, ip; 200 mg/kg 5-FU ip; or 200 mg/kg 5-FU ip 6000 mg/kg TK-90 administered in an osmotic pump over 24 hours starting 4 hours post 200 mg/kg 5-FU ip. Eight mice were dosed per treatment group. Plasma citrulline is a marker for mucosal health. (Jones et al., "Citrulline as a Biomarker in the Murine Total-Body Irradiation Model: Correlation of Circulating and Tissue Citrulline to Small Intestine Epithelial Histopathology," Health Phys. (2015) 109(5): 452-65). Plasma citrulline is lowered with mucositis. (Fragkos et al., "Citrulline as a marker of intestinal function and absorption in clinical settings: A systematic review and meta-analysis," United European Gastroenterol J. (2018) 6(2):181-191). TK-90 reverses the decrease in plasma citrulline caused by the 5-FU.

Thawed plasma samples from the study were analyzed for citrulline using a published LC/MS/MS-Isotope assay. (Jones et al., Development and validation of a LC-MS/MS assay for quantitation of plasma citrulline for application to animal models of the acute radiation syndrome across multiple species," Anal Bioanal Chem. (2014) 406(19):4663-75). Summary results provided as mean citrulline concentrations (μMolar) are provided in FIG. 4. Compared to the PBS vehicle control (blue), the 5-FU treatment (red) provided a significant reduction in citrulline. However, the TK-90 treatment (green) provided a robust, statistically significant rebound in plasma citrulline compared to the 5-FU group alone (p<0.001 for Groups 2 and 3.

A representative 2,2'-anhydropyrimidine test article provided statistically significant protection from the lowered plasma citrulline, a widely accepted sign of mucositis.

IV. Protection by a 2,2'-Anhydropyrimidine Test Article from Changes in Plasma Cytokines Considered Related to Mucositis The chemotherapeutic challenge was cytokine changes induced by 5-FU treatment.

Figure 5:
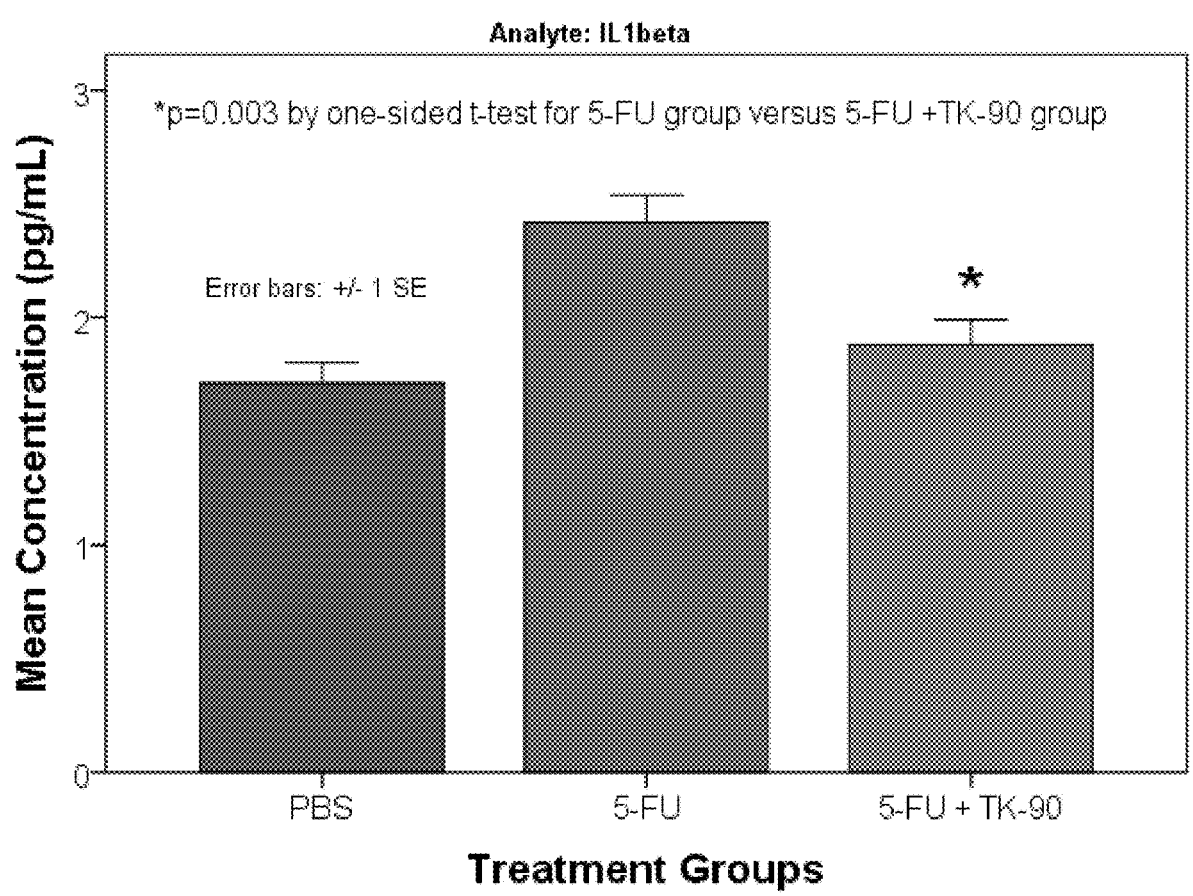
FIG. 5 depicts IL-1β was measured in plasma obtained at sacrifice on Day 3 from C57BL6 female mice treated on Day 0 with either PBS, ip; 200 mg/kg 5-FU, ip; or 200 mg/kg 5-FU, ip, plus 6000 mg/kg TK-90 administered in an osmotic pump over 24 hours starting 4 hours post 5-FU dose. Eight C57BL6 mice were dosed per treatment. TK-90 reverses the increase in plasma IL-1β caused by the 5-FU.
Figure 6:
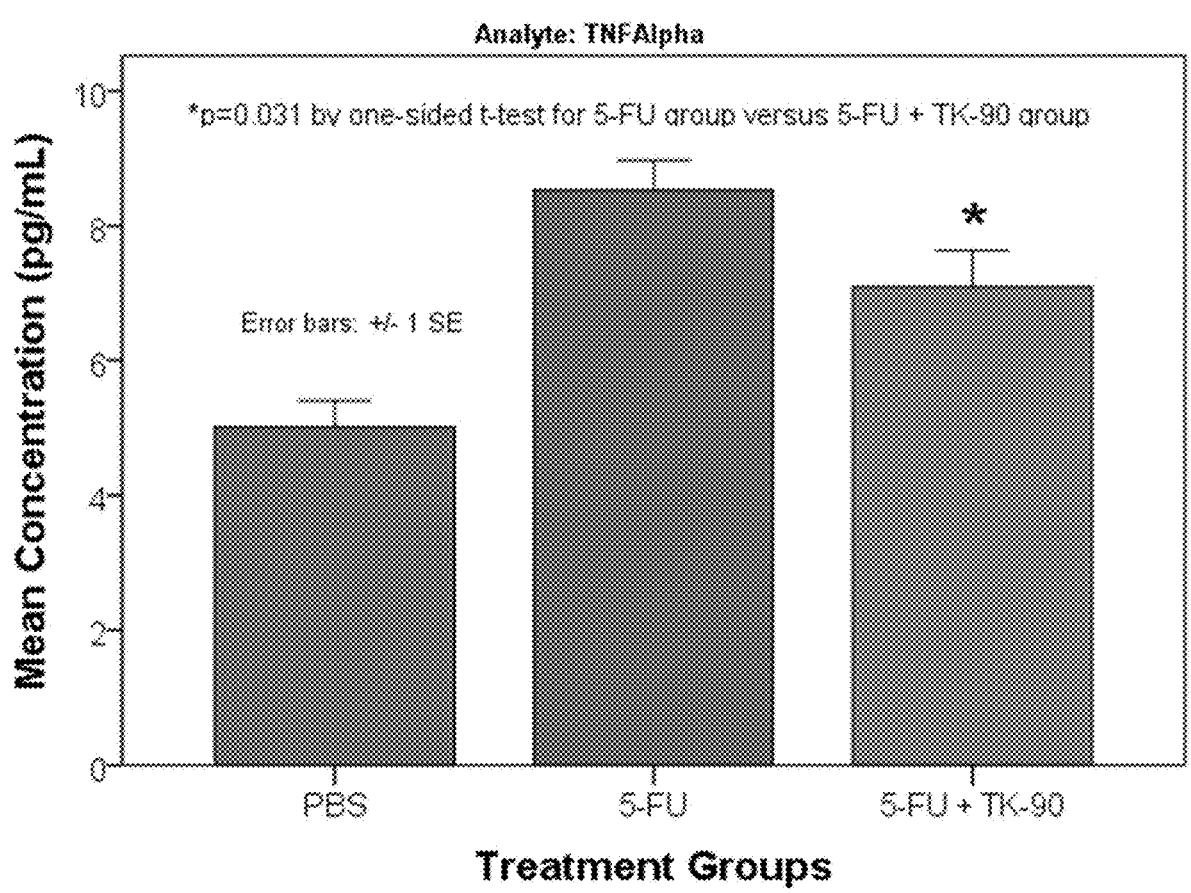
FIG. 6 depicts TNF-α concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma TNF-α caused by the 5-FU.
Figure 7:
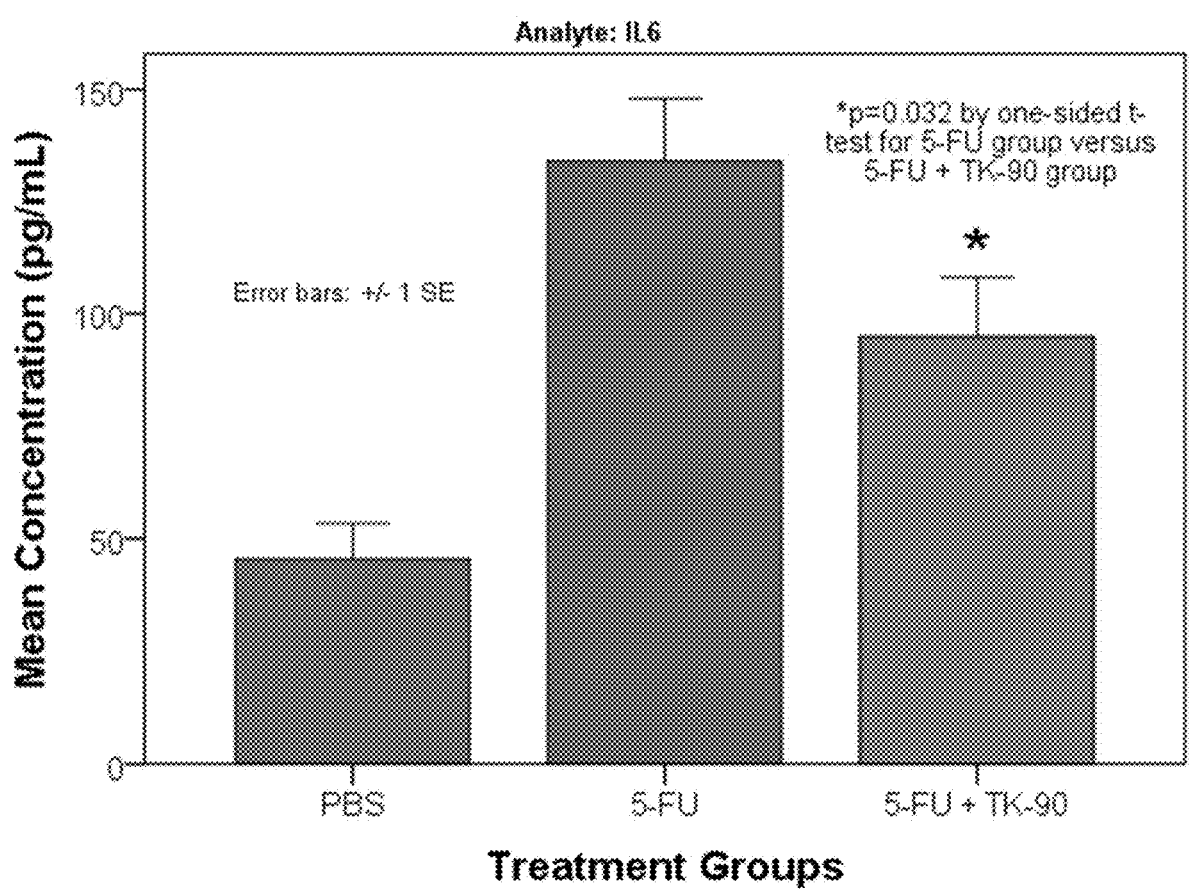
FIG. 7 depicts IL-6 concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma IL-6 caused by the 5-FU.
Figure 8:
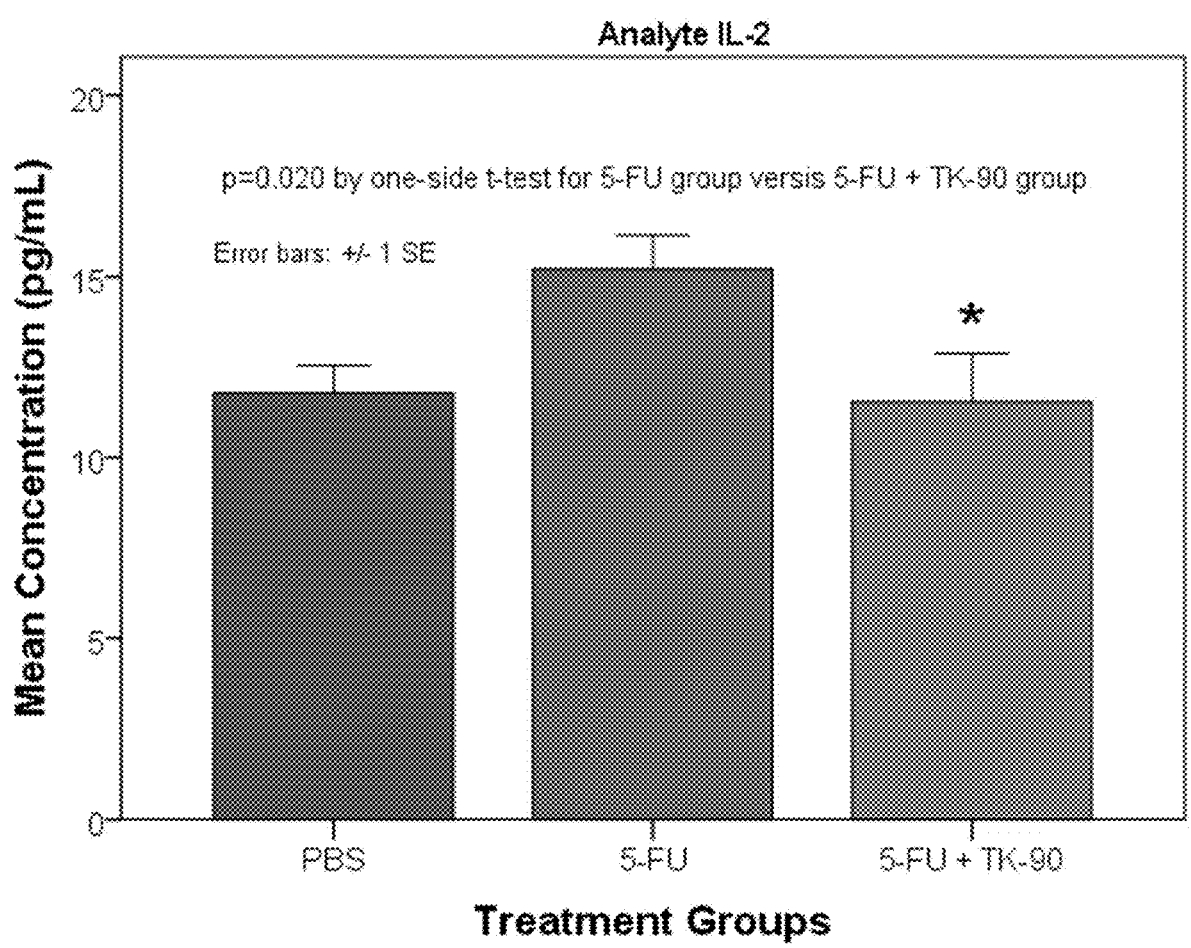
FIG. 8 depicts IL-2 concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma IL-2 caused by the 5-FU.
Figure 9:
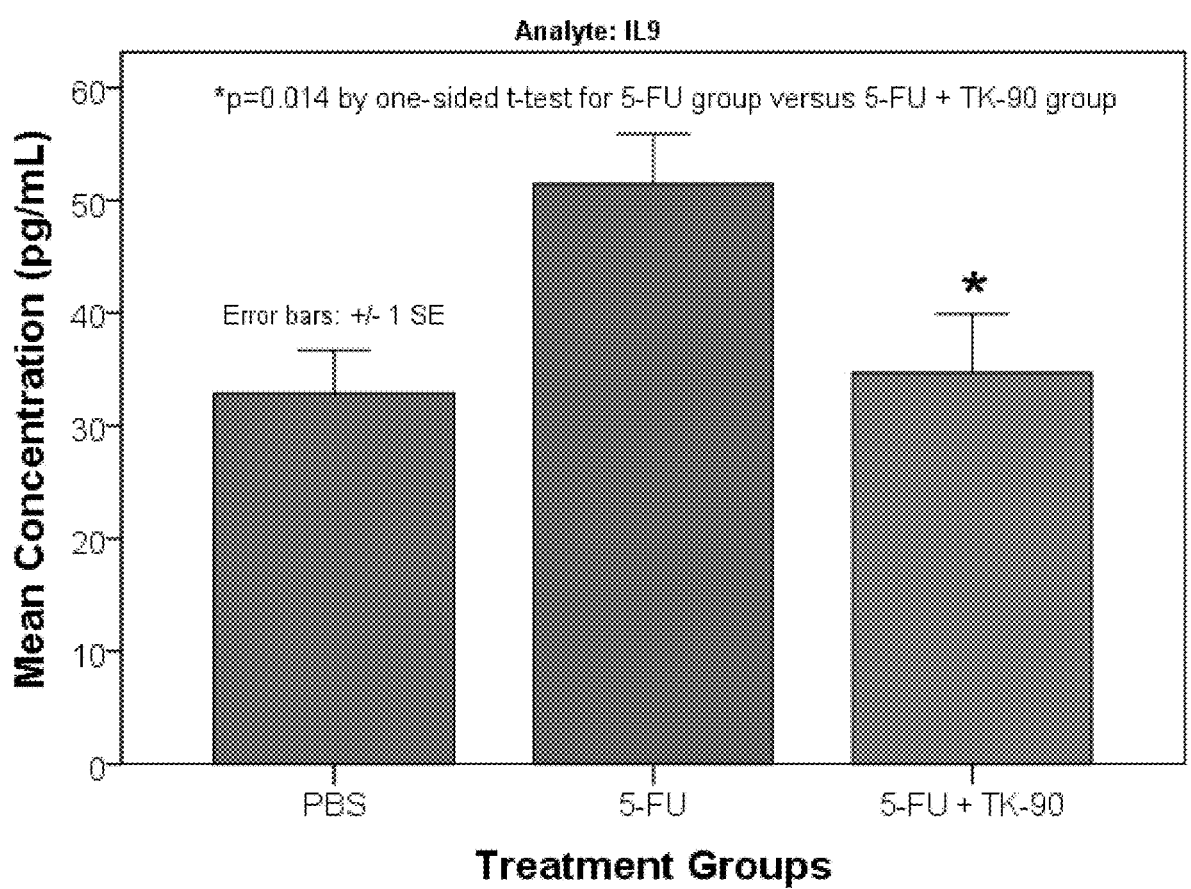
FIG. 9 depicts IL-9 concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma IL-9 caused by the 5-FU.
Figure 10:
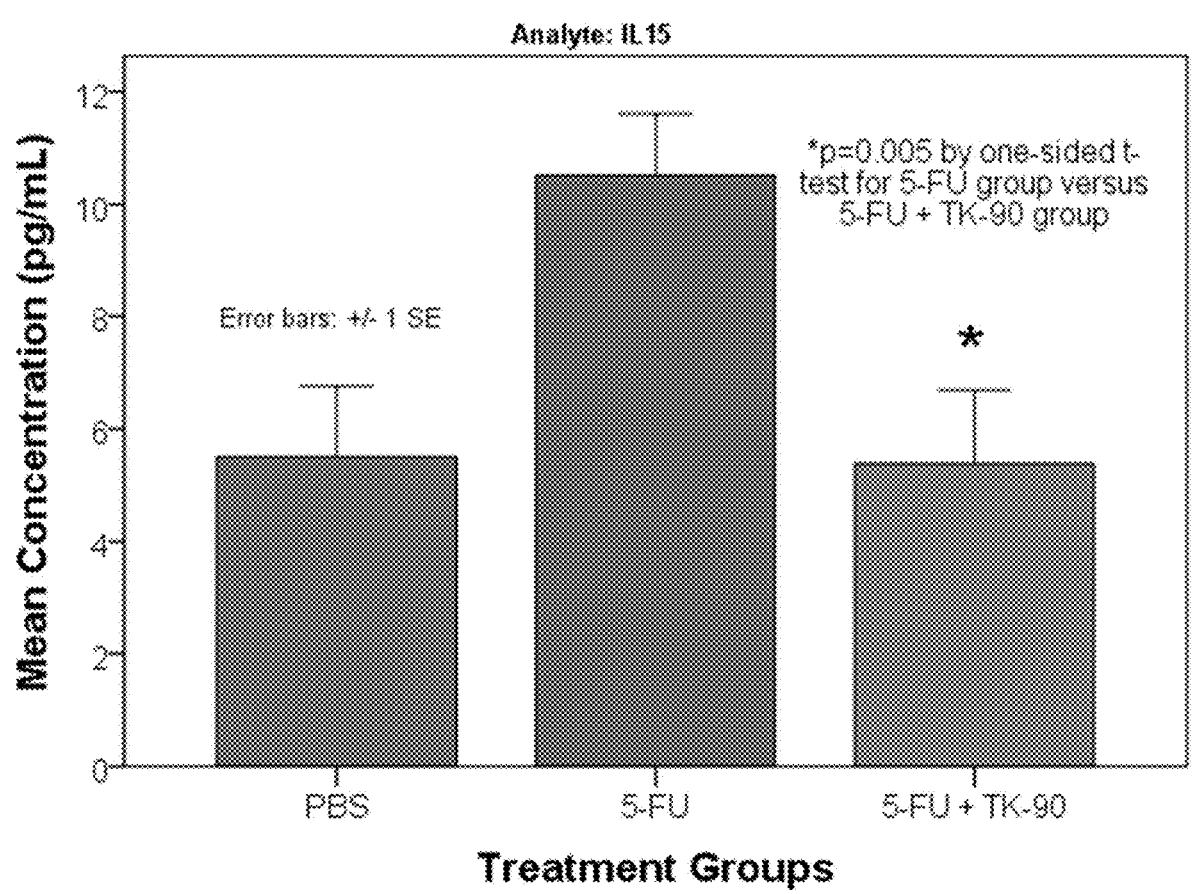
FIG. 10 depicts IL-15 concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma IL-15 caused by the 5-FU.
Figure 11:
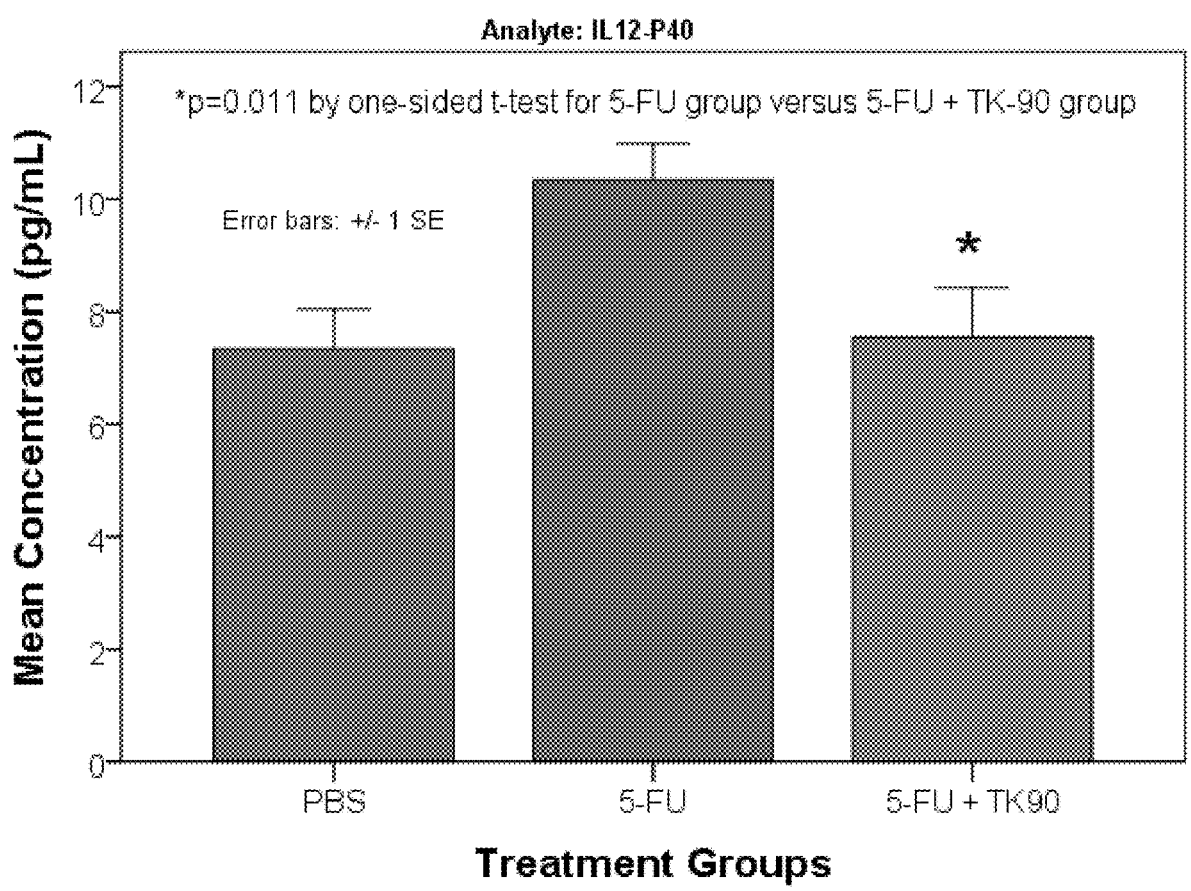
FIG. 11 depicts IL-12 (P40) concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma IL-12 (P40) caused by the 5-FU.
Figure 12:
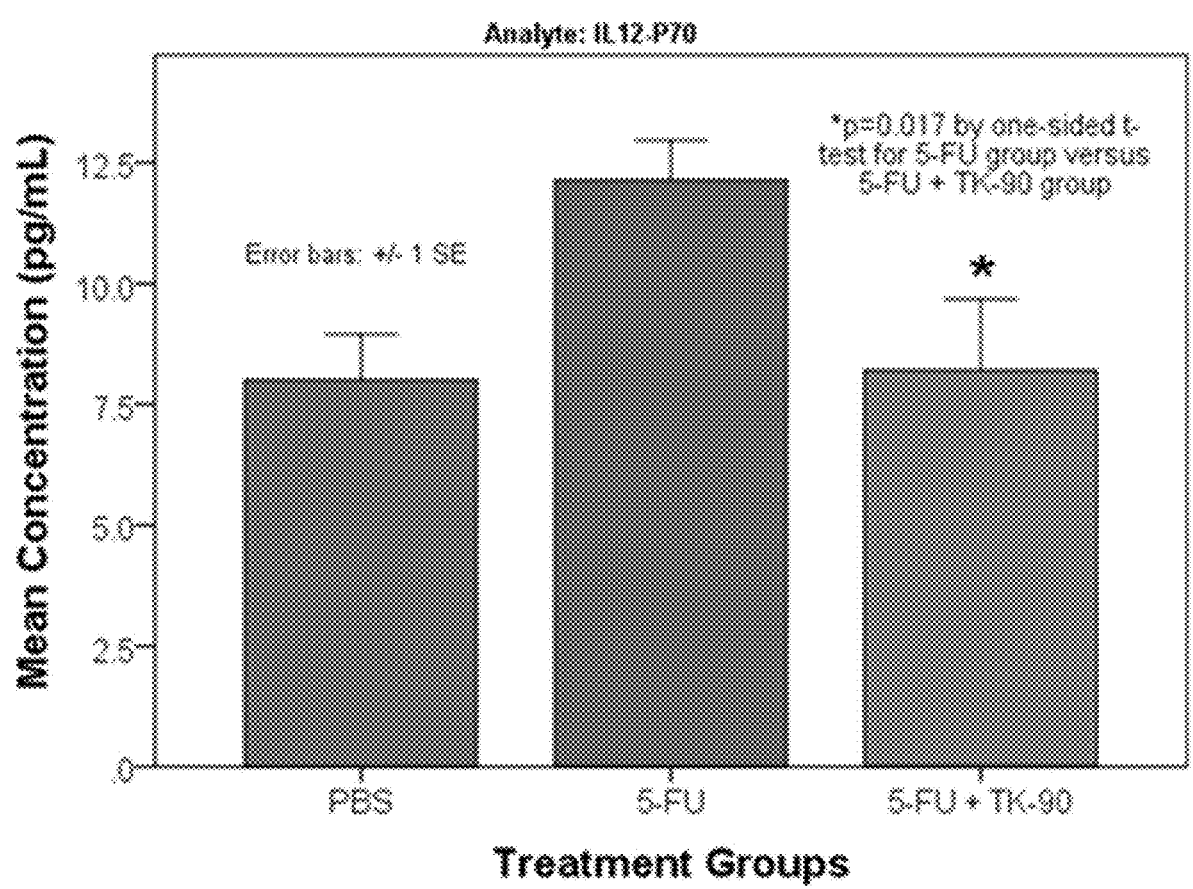
FIG. 12 depicts IL-12 (P70) concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma IL-12 (P70) caused by the 5-FU.
Figure 13:
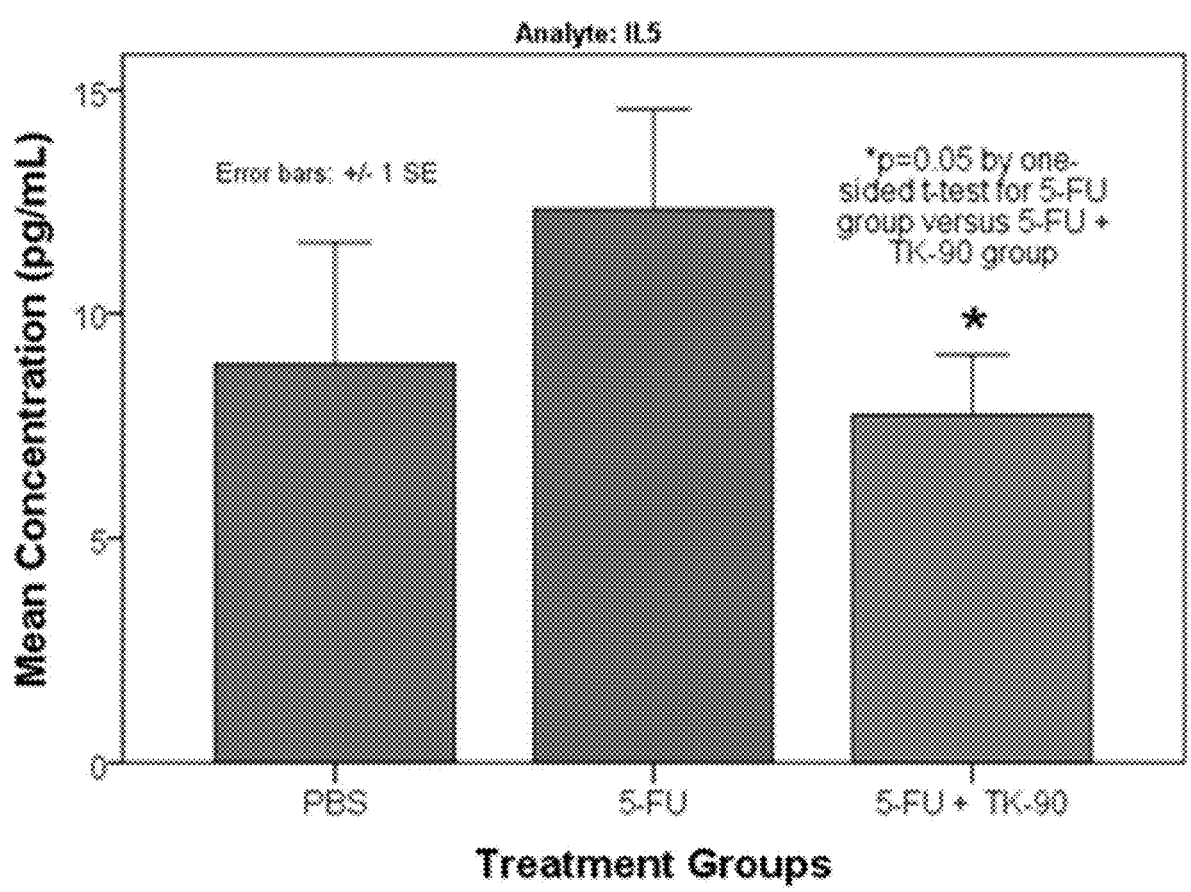
FIG. 13 depicts IL-5 concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma TNF-α caused by the 5-FU
Figure 14:
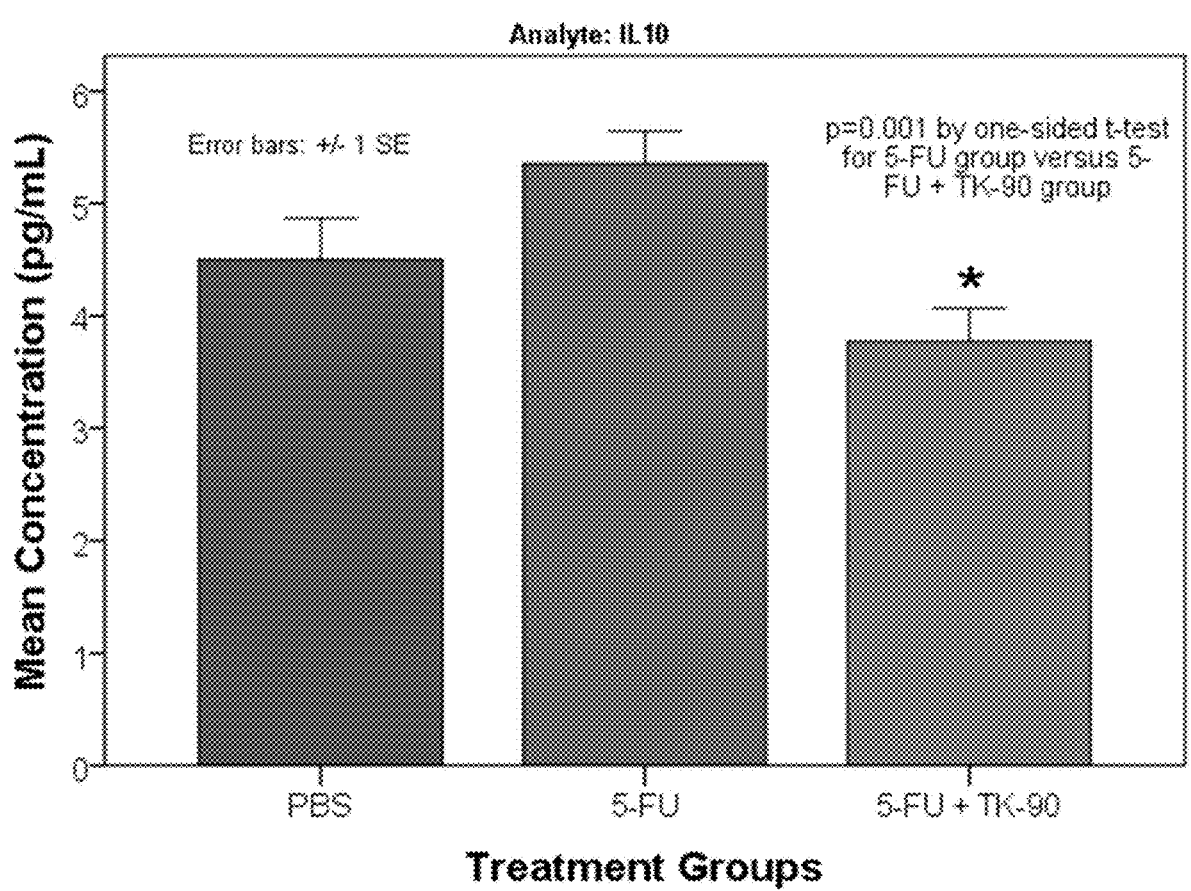
FIG. 14 depicts IL-10 concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma IL-10 caused by the 5-FU.
Figure 15:
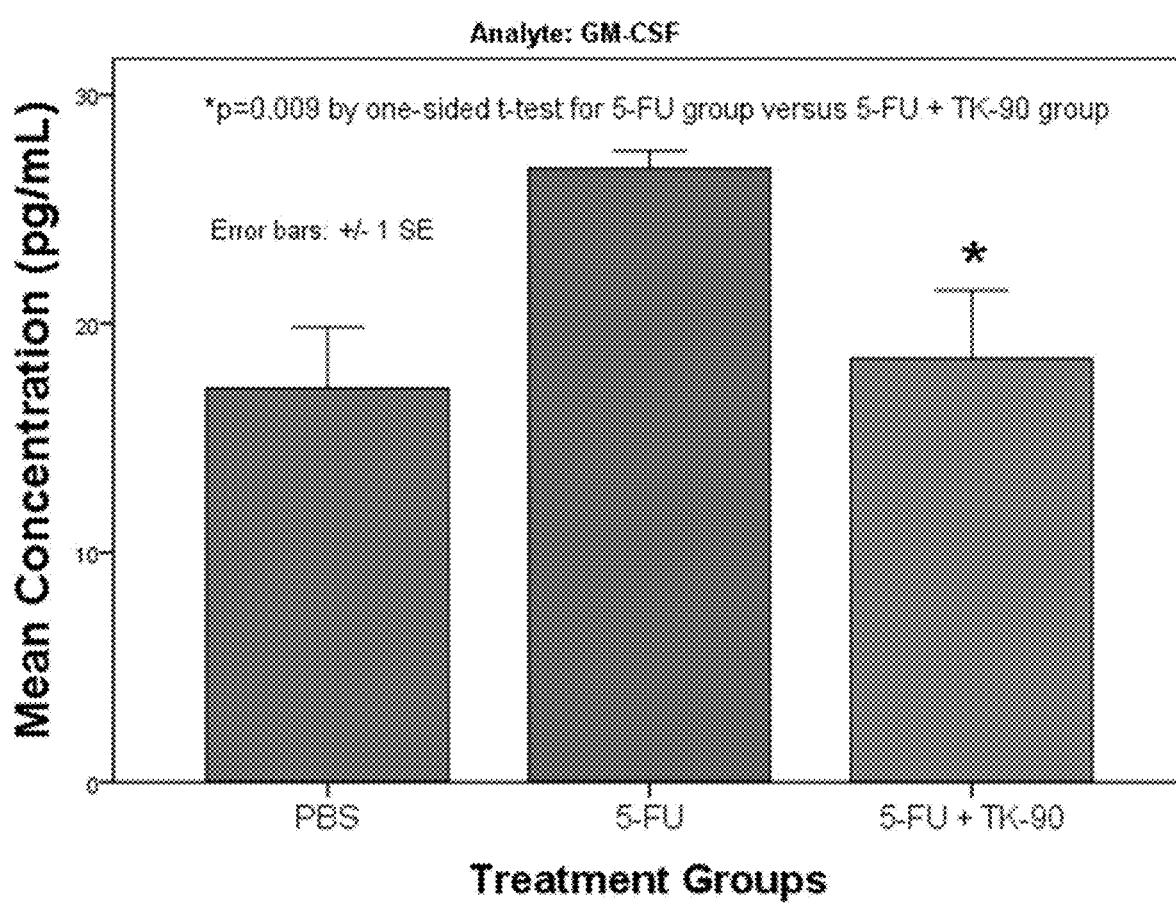
FIG. 15 depicts GM-CSF concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma GM-CSF caused by the 5-FU.
Figure 16:
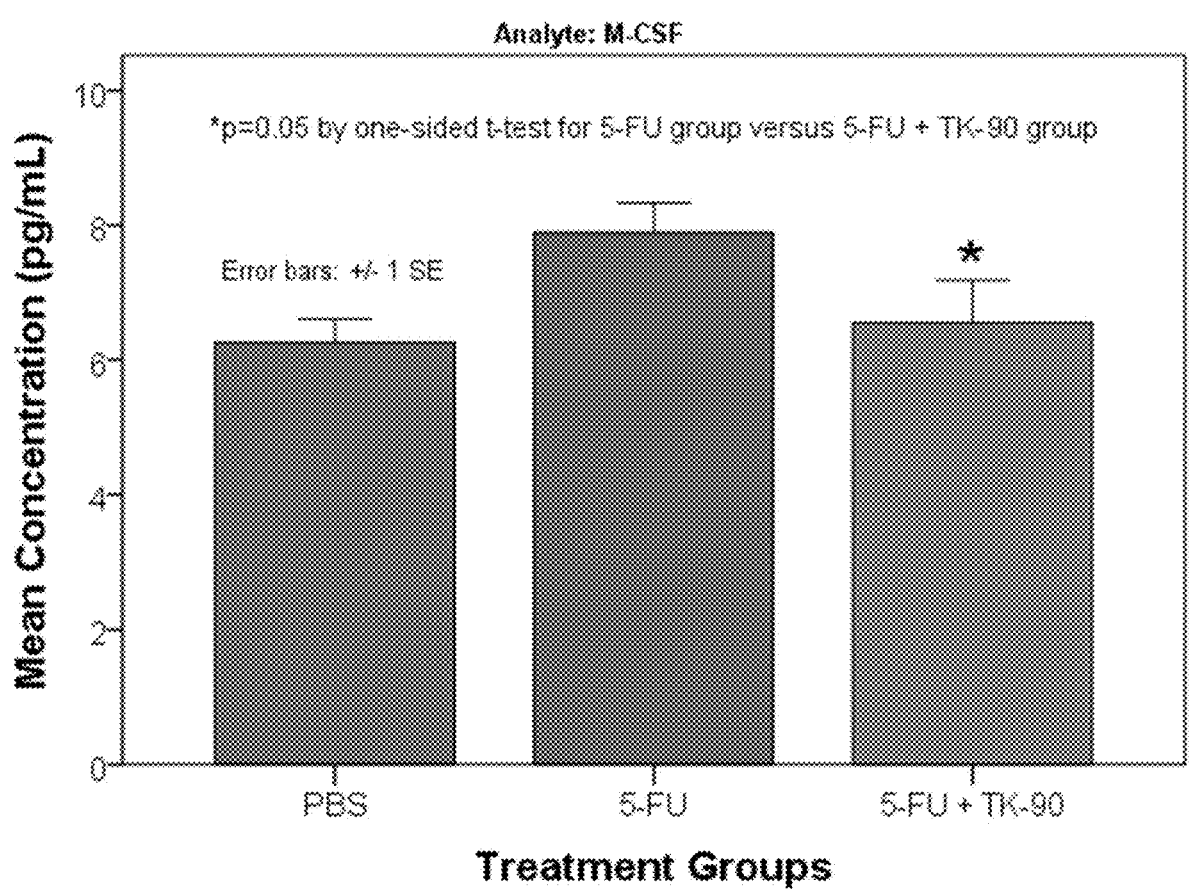
FIG. 16 depicts M-CSF concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma M-CSF caused by the 5-FU.
Figure 17:
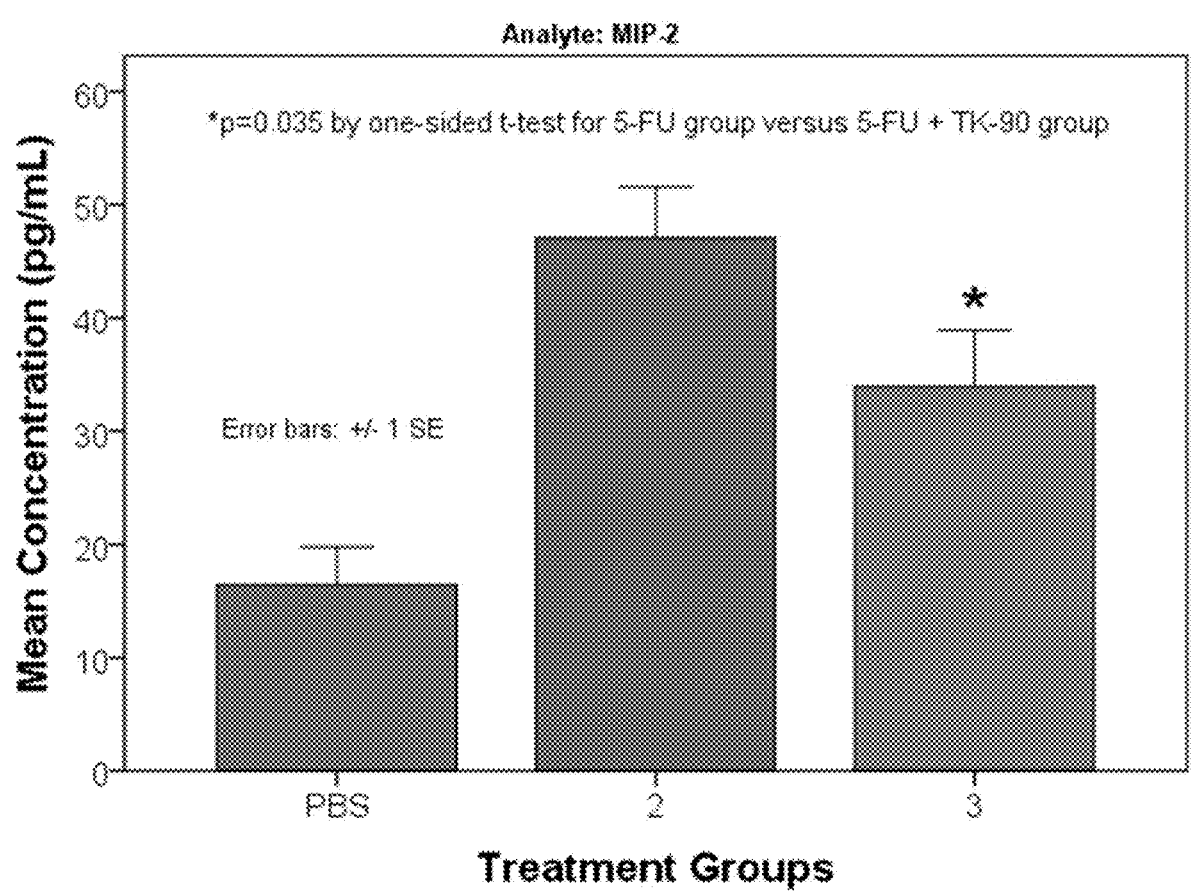
FIG. 17 depicts MIP-2 concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma MIP-2 caused by the 5-FU.
Figure 18:
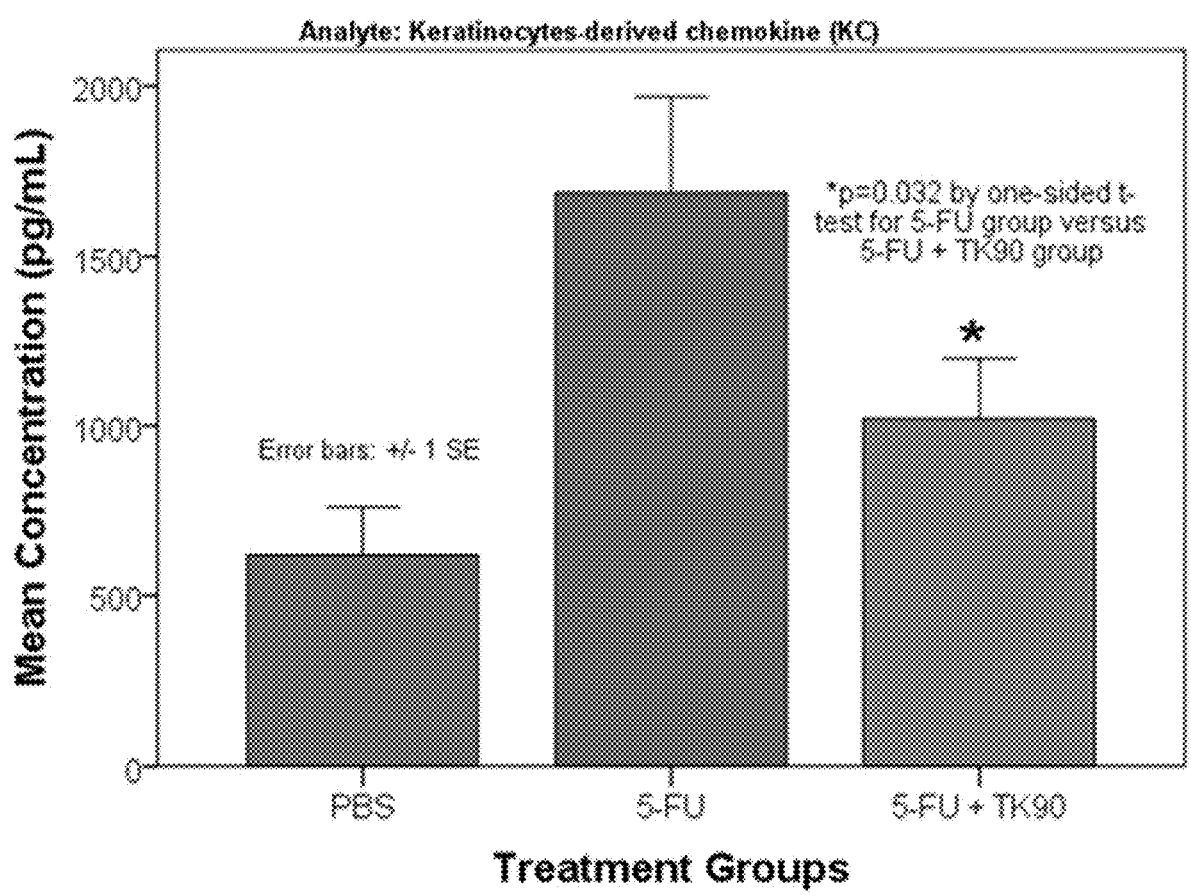
FIG. 18 depicts KC concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the increase in plasma KC caused by the 5-FU.
Figure 19:
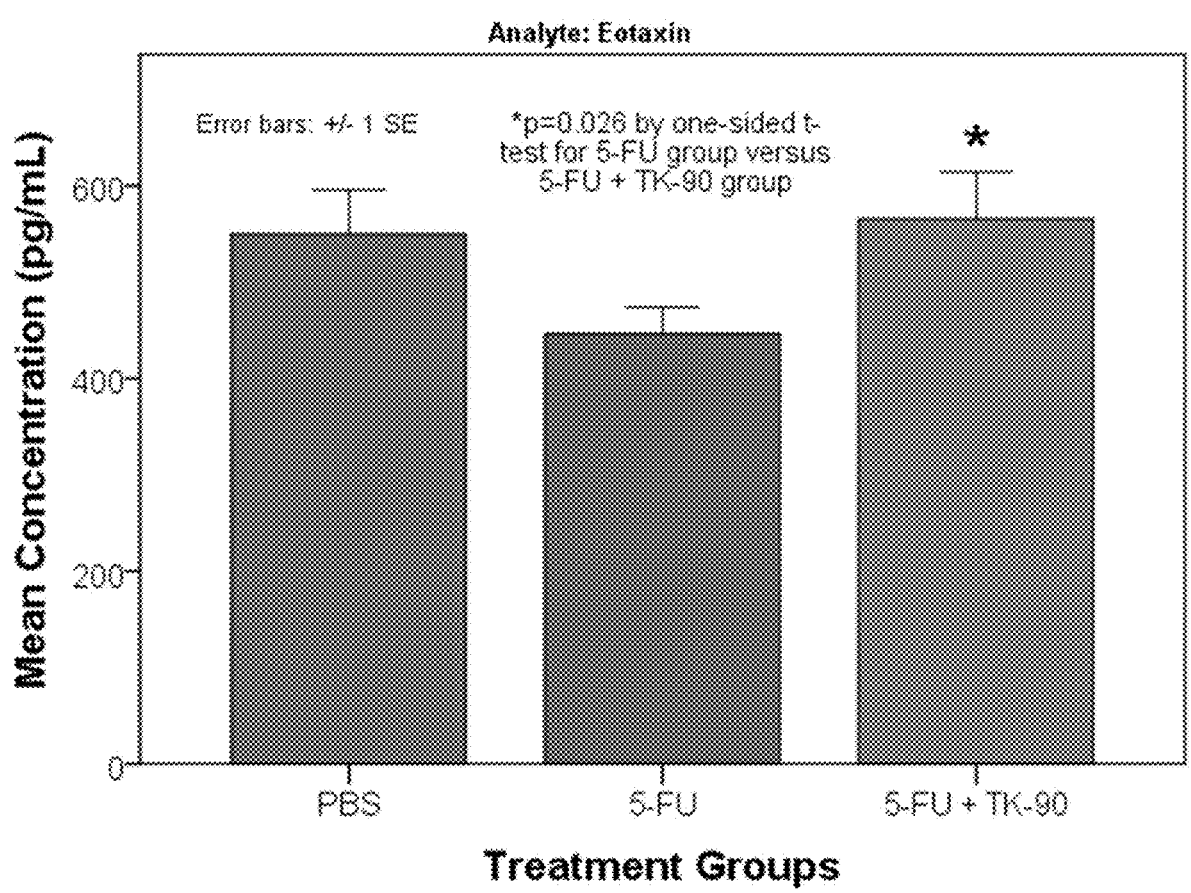
FIG. 19 depicts eotaxin concentrations measured in plasma obtained at sacrifice on Day 3 from C57BL6 female mice treated on Day 0 with either PBS, ip; 200 mg/kg 5-FU, ip; or 200 mg/kg 5-FU ip plus 6000 mg/kg TK-90 administered in an osmotic pump over 24 hours starting 4 hours post 5-FU dose. Eight C57BL/6 mice were dosed per treatment. TK-90 reverses the decrease in plasma eotaxin caused by the 5-FU.

Plasma samples from Experiment III were analyzed for a panel of cytokines and related biochemicals by multiplex ELISA. Cytokines with highly significantly different for the 5-FU and 5-FU+TK-90 groups were: IL-1B, IL-2, IL-9, IL-10, IL-12 (p40), IL-12 (p70), IL-15, and GM-CSF. Cytokines with significantly different for the 5-FU and 5-FU+TK-90 groups were: IL-5, IL-6, keratinocytes-derived chemokine (KC), M-CSF, MIP-2, TNFα and eotaxin. IL-1B, TNF-α, and IL-6 are pro-inflammatory cytokines known to be elevated with mucositis. (Logan et al., "The role of pro-inflammatory cytokines in cancer treatment-induced alimentary tract mucositis: pathobiology, animal models and cytotoxic drugs," Cancer Treat Rev. (2007) 33(5):448-60; Ong et al., "Pro-inflammatory cytokines play a key role in the development of radiotherapy-induced gastrointestinal mucositis," Radiat Oncol. (2010) (16) 5:22). TK-90 reverses elevation of all three of these cytokines (FIGS. 5, 6 and 7). IL-2 is a pleiotropic cytokine that drives growth and activation of inflammatory cells such as T-cells, NK cells, etc. IL-9 and IL-15 signal through IL-2. TK-90 reverse the 5-FU induced elevation of all three of these cytokines (FIGS. 8, 9, and 10). IL-12 is a cytokine linked to generation of an immune response. Another cytokine associated with generation of an immune response is IL-5. TK-90 reverse the 5-FU induced elevation of IL-12 and IL5 (FIGS. 11, 12 and 13). IL-10 is a cytokine that plays a central role in limiting host immune response. TK-90 reverses the elevation of IL-10 induced by the 5-FU treatment possibly allowing an immune response to proceed to potentially clear damaged tissue (FIG. 14). GM-CSF and M-CSF both stimulate cell mediators of inflammation. TK-90 reverse the 5-FU induced elevation of both GM-CSF and G-CSF (FIGS. 15 and 16). MIP-2, and KC are chemokines that function much like GM-CSF, and M-CSF to stimulate cell mediators of inflammation TK-90 reverse the 5-FU induced elevation of the chemokines (FIGS. 17 and 18). 5-FU decreases eotaxin, a chemokine that recruits immune-related mediators like eosinophils into inflammatory sites (FIG. 19). TK-90 reverses this decrease.

It is evident from the above results that the subject invention provides for methods of reducing the toxicity of 5-FU treatment while retaining desired chemotherapeutic activity. Both the undesirable inflammatory and immune response induced by the 5-FU are reduced. The toxicity reduction is such that the invention finds use in a variety of different applications and represents a significant contribution to the art.

Although the foregoing invention has been described in some detail by way of illustration and example for purposes of clarity of understanding, it is readily apparent to those of ordinary skill in the art considering the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of treating a subject for mucositis, the method comprising:
administering to a subject known to be suffering from mucositis an effective amount of a 2,2'-anhydropyrimidine or derivative thereof in combination with an effective amount of uridine to treat the subject for mucositis.

2. The method according to claim 1, wherein the 2,2'-anhydropyrimidine or derivative thereof is a compound of formula (I):

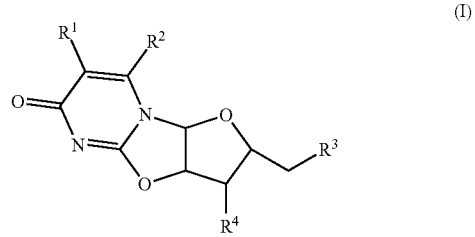

or the pharmaceutically acceptable salts, solvates, hydrates, and prodrug forms thereof, and stereoisomers thereof, wherein:
each $R^1$, $R^2$, $R^3$ and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, halogen or pseudohalogen, carbohydrate, nucleic acid, amino acid, peptide, dye, fluorophore and polypeptide.

3. The method according to claim 2, wherein each $R^1$, $R^2$, $R^3$ and $R^4$ is independently selected from the group consisting of hydrogen, hydroxyl, sulfhydryl, amino, hydroxymethyl, methoxy, halogen, pseudohalogen, and a substituted or unsubstituted lower hydrocarbon containing 1 to 20 carbons.

4. The method according to claim 3, wherein the lower hydrocarbon is selected from the group consisting of alkyl, alkenyl, alkanoyl, aryl, aroyl, aralkyl and alkylamino, and esters thereof.

5. The method according to claim 2, wherein $R^1$ is hydrogen, fluorine, methyl, ethyl, propyl, benzyl, or 2-bromovinyl; $R^2$ is hydrogen, hydroxyl fluorine, methyl, ethyl, propyl, benzyl, benzoyl, benzoyloxy, or 2-bromovinyl; and each $R^3$ and $R^4$ is independently selected from the group consisting of hydroxyl and benzoyloxy.

6. The method according to claim 5, wherein $R^1$ is hydrogen or methyl; $R^2$ is hydrogen; and each $R^3$ and $R^4$ is independently selected from the group consisting of hydroxyl and benzoyloxy.

7. The method according to claim 1, wherein the 2,2'-anhydropyrimidine or derivative thereof is selected from the group consisting of: 2,2'-anhydro-5-methyluridine; 3'-O-benzoyl-2,2'-anhydrouridine; 3'-O-benzoyl-2,2'-anhydro-5-methyluridine; 5'-O-benzoyl-2,2'-anhydrouridine; and 5'-O-benzoyl-2,2'-anhydro-5-methyluridine.

8. The method according to claim 7, wherein the 2,2'-anhydropyrimidine or derivative thereof is 2,2'-anhydro-5-methyluridine.

9. The method according to claim 7, wherein the 2,2'-anhydropyrimidine or derivative thereof is 3'-O-benzoyl-2,2'-anhydro-5-methyluridine.

10. The method according to claim 7, wherein the 2,2'-anhydropyrimidine or derivative thereof is 5'-O-benzoyl-2,2'-anhydro-5-methyluridine.

11. The method according to claim 1, wherein the 2,2'-anhydropyrimidine or derivative thereof comprises a stereoisomer.

12. The method according to claim 11, wherein the stereoisomer is selected from the group consisting of 2,2'-anhydro-1-(β-D-arabinofuranosyl)-5-methyluracil; 3'-O-benzoyl-2,2'-anhydro-1-(β-D-arabinofuranosyl)-uracil; 3'-O)-benzoyl-2,2'-anhydro-1-(β-D-arabinofuranosyl)-5-methyluracil; 5'-O-benzoyl-2,2'-anhydro-1-(β-D-arabinofuranosyl)-uracil; and 5'-O-benzoyl-2,2'-anhydro-1-(β-D-arabinofuranosyl)-5-methyluracil.

13. The method according to claim 1, wherein the 2,2'-anhydropyrimidine or derivative thereof and the uridine are administered at the same time.

14. The method according to claim 13, wherein the 2,2'-anhydropyrimidine or derivative thereof and the uridine are administered as separate formulations.

15. The method according to claim 13, wherein the 2,2'-anhydropyrimidine or derivative thereof and the uridine are administered in a single formulation.

16. The method according to claim 1, wherein the 2,2'-anhydropyrimidine or derivative thereof and the uridine are administered sequentially.

17. The method according to claim 1, wherein the method further comprises administering a second UPase inhibitor.

18. The method according to claim 1, wherein the mucositis is stomatitis.

19. The method according to claim 1, wherein the subject is undergoing cancer therapy.

20. The method according to claim 19, wherein in the cancer therapy is selected from the group consisting of radiation therapy, chemotherapy and combinations thereof.

* * * * *

UNITED STATES PATENT AND TRADEMARK OFFICE
CERTIFICATE OF CORRECTION

PATENT NO. : 12,109,222 B2
APPLICATION NO. : 17/175258
DATED : October 8, 2024
INVENTOR(S) : William A. Garland et al.

It is certified that error appears in the above-identified patent and that said Letters Patent is hereby corrected as shown below:

In the Specification

Please replace "PLOS" with -- PLoS -- (Column 3, Line 6).

Please replace "(1 uridine" with -- (↑ uridine -- (Column 3, Line 17).

Please replace "—S—," with -- —S$^-$, -- (Column 10, Line 7).

Please replace "—S(O)$_{20}$," with -- —S(O)$_2$O$^-$, -- (Column 10, Line 9).

Please replace "—OS(O$_2$)O—," with -- —OS(O$_2$)O$^-$, -- (Column 10, Line 10).

Please replace "—P(O)(O—)$_2$," with -- —P(O)(O$^-$)$_2$, -- (Column 10, Line 10).

Please replace "—P(O)(OR$^8$)(O—)," with -- —P(O)(OR$^8$)(O$^-$), -- (Column 10, Line 11).

Please replace "—C(O)O," with -- —C(O)O$^-$, -- (Column 10, Line 12).

Please replace "—NR$^{10}$C(O)NR$^8$R$^9$, —NR$^{10}$C(S)NR$^8$R$^9$," with -- —NR$^{10}$C(O)NR$^8$R$^9$, —NR$^{10}$C(S)NR$^8$R$^9$, -- (Column 10, Line 13).

Please replace "aryoloxy" with -- aroyloxy -- (Column 16, Line 7).

Please replace "aryoloxy," with -- aroyloxy, -- (Column 16, Line 26).

Please replace "aryoloxy" with -- aroyloxy -- (Column 16, Line 46).

Please replace "aryoloxy" with -- aroyloxy -- (Column 17, Line 27).

Please replace "adamantyl," with -- adamantoyl, -- (Column 17, Line 31).

Signed and Sealed this
Thirty-first Day of December, 2024

Derrick Brent
*Acting Director of the United States Patent and Trademark Office*

CERTIFICATE OF CORRECTION (continued)
U.S. Pat. No. 12,109,222 B2

Please replace "adamantyl." with -- adamantoyl. -- (Column 17, Line 31).

Please replace "aryoloxy," with -- aroyloxy, -- (Column 17, Line 35).

Please replace "aryoloxy" with -- aroyloxy -- (Column 17, Line 54).

Please replace "aryoloxy)" with -- aroyloxy) -- (Column 18, Line 19).

Please replace "aryoloxy." with -- aroyloxy. -- (Column 18, Line 33).

Please replace "aryoloxy," with -- aroyloxy, -- (Column 22, Line 59).

Please replace "heteroaryoloxy," with -- heteroaroyloxy, -- (Column 22, Line 59).

Please replace "aryoloxy," with -- aroyloxy, -- (Column 24, Line 8).

Please replace "heteroaryoloxy," with -- heteroaroyloxy, -- (Column 24, Line 9).

Please replace "IL-1B," with -- IL-1β, -- (Column 39, Line 21).

Please replace "IL-1B," with -- IL-1β, -- (Column 39, Line 25).

In the Claims

Please replace "3'-O)" with -- 3'-O -- (Column 42, Line 14).

Please replace "anbydropyrimidine" with -- anhydropyrimidine -- (Column 42, Line 19).

Please replace "anbydropyrimidine" with -- anhydropyrimidine -- (Column 42, Line 28).